United States Patent [19]
Bright et al.

[11] Patent Number: 5,157,034
[45] Date of Patent: Oct. 20, 1992

[54] NEUROLEPTIC PERHYDRO-1H-PYRIDO[1,2-A]PYRAZINES

[75] Inventors: Gene M. Bright, Groton; Kishor A. Desai, Ledyard; Thomas F. Seeger, Mystic, all of Conn.

[73] Assignee: Pfizer Inc., New York, N.Y.

[21] Appl. No.: 661,791

[22] Filed: Feb. 27, 1991

[51] Int. Cl.$^5$ .................. C07D 487/04; C07D 211/60; C07D 211/62; A61K 31/495
[52] U.S. Cl. .................... 514/249; 514/211; 540/524; 544/230; 544/349; 546/326
[58] Field of Search ............... 540/524; 544/230, 349; 514/211, 249

[56] References Cited

U.S. PATENT DOCUMENTS

| | | | |
|---|---|---|---|
| 4,681,938 | 7/1987 | Traxler | 544/349 |
| 4,831,031 | 5/1989 | Lowe, III et al. | 514/254 |
| 4,957,916 | 9/1990 | Kennis et al. | 514/254 |

FOREIGN PATENT DOCUMENTS

WO90/08144  7/1990  PCT Int'l Appl.

*Primary Examiner*—Mark L. Berch
*Attorney, Agent, or Firm*—Peter C. Richardson; J. Trevor Lumb; D. Stuart McFarlin

[57] ABSTRACT

Antipsychotic compounds having the formula

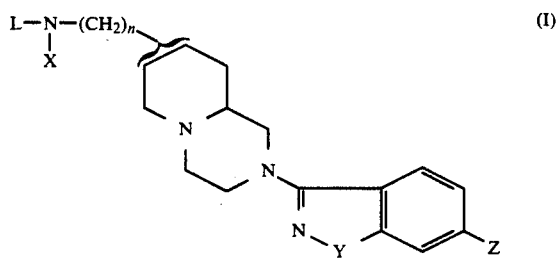

wherein Z is H or Cl; Y is O or S; n is 1-4; separately, X is H or $(C_1-C_2)$alkyl and L is $R(CH_2)_mCO$, m is 0 or 1-3, R is $(C_1-C_6)$alkyl, $(C_3-C_7)$cycloalkyl, phenyl, naphthyl, furyl, benzofuranyl, thienyl, benzothienyl, pyrrolyl, indolyl, isoindolyl or one of said groups substituted on aromatic or heteroaromatic ring with fluoro, chloro, $(C_1-C_2)$alkyl or $(C_1-C_2)$alkoxy; or together L and X, in combination with the nitrogen to which they are attached, form certain cyclic imides, 4-substituted piperidines or a cyclic sulfonamide.

68 Claims, No Drawings

NEUROLEPTIC PERHYDRO-1H-PYRIDO[1,2-A]PYRAZINES

BACKGROUND OF THE INVENTION

The present invention is directed to certain perhydro-1H-pyrido[1,2-a]pyrazines which are depicted by the formula (I) and defined below; to pharmaceutical compositions and a method of treating psychotic diseases therewith; and to certain intermediates useful in the synthesis thereof.

Structurally related perhydro-1H-pyrido[1,2-a]-pyrazines of the formula

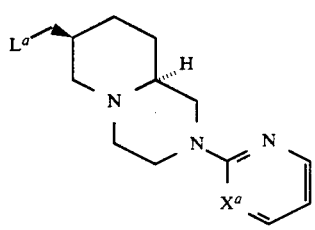

(A)

wherein X is N or CH and $L^a$ represents one of certain pyrazolo, triazolo, tetrazolo or cyclic imido radicals have been reported to possess useful anxiolytic activity, Bright and Desai, International Application published under the PCT as publication No. WO 90/08144.

A variety of compounds are reported to be in possession of neuroleptic activity useful in the treatment of psychotic diseases. These include piperidine derivatives of the formula

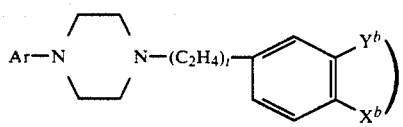

(B)

wherein t is 1 or 2, Ar is naphthyl or one of a variety of bicyclic heteroaryl groups, including benzisothiazoyl, and $X^b$ and $Y^b$ together with the attached phenyl group form a similar such bicyclic heteroaryl group (Lowe III et al., U.S. Pat. No. 4,831,031); and compounds of the formula

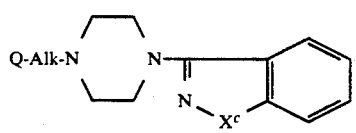

(C)

wherein Q represents certain bicyclic heteroaryl groups, Alk is alkanediyl and $X^c$ represents O, S, NH, or substituted NH (Kennis et al., U.S. Pat. No. 4,957,916).

SUMMARY OF THE INVENTION

The present invention is directed to both racemic and optically active perhydro-1H-pyrido[1,2-a]pyrazines having the formula

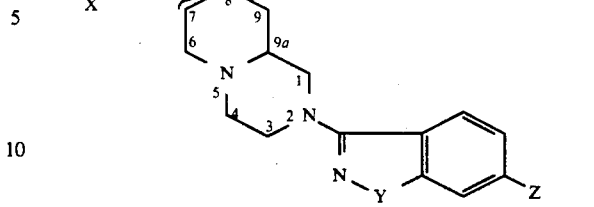

(I)

wherein

Z is H or Cl;

Y is O or S;

n is 1, 2, 3 or 4; and

L and X are taken separately, X is H or $(C_1-C_2)$alkyl and L is $R(CH_2)_mCO$ where m is 0, 1, 2 or 3 and R is $(C_1-C_6)$alkyl, $(C_3-C_7)$cycloalkyl, phenyl, naphthyl, furyl, benzofuranyl, thienyl, benzothienyl, pyrrolyl, indolyl, isoindolyl or one of said groups substituted on aromatic or heteroaromatic ring with fluoro, chloro, $(C_1-C_2)$alkyl or $(C_1-C_2)$alkoxy; or L and X are taken together and are:

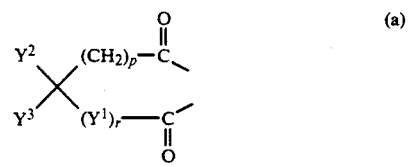

(a)

where $Y^1$ is $CH_2$, S, O or NH; $Y^2$ and $Y^3$ are taken separately and $Y^2$ and $Y^3$ are reach independently hydrogen or methyl, or $Y^2$ and $Y^3$ are taken together and are $(CH_2)_q$; p is 1 or 2, q is 2, 3, 4 or 5; and r is 0 or 1;

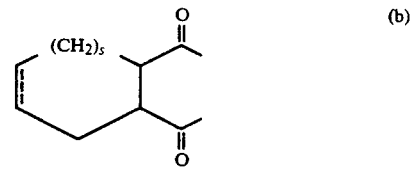

(b)

where s is 0 or 1; and - - - represents a bond or no bond;

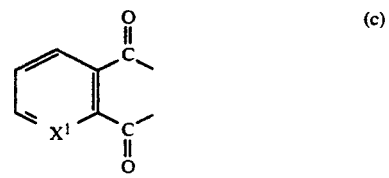

(c)

where $X^1$ is CH or N;

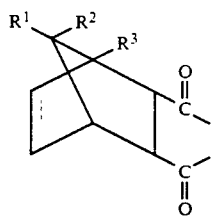

(d)

where $R^1$, $R^2$ and $R^3$ are each independently H or $CH_3$ and - - - represents a bond or no bond;

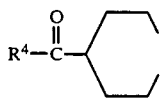

(e)

where $R^4$ is phenyl or phenyl substituted with F, Cl, $(C_1-C_2)$alkyl or $(C_1-C_2)$ alkoxy;

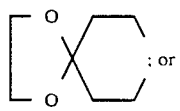

(f)

; or

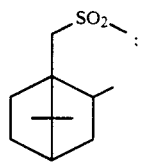

(g)

or a pharmaceutically acceptable acid addition salt thereof.

In these compounds, the group substituted at the 7- or 8-position of the pyridopyrazine ring system can be either cis or trans to the 9a-hydrogen. When the substituent is at the 8-position, because of their ease of preparation and generally better activity, preferred compounds generally have the 8-position substituent and 9a-hydrogen trans to one another, or, alternatively stated, the 8- and 9a-hydrogen atoms are cis to each other. Preferred values of Y and Z are generally oxygen and hydrogen. When L and X are taken separately, the preferred value of X is hydrogen and the preferred values of L are $R(CH_2)_nCO$ where R is phenyl or $(C_3-C_6)$cycloalkyl and n is 1 or 2. When L and X are taken together, the preferred value of L and X corresponds to above partial formula (a), particularly those compounds wherein $Y^1$ is $CH_2$, p and r are each 1 and $Y^2$ and $Y^3$ are taken together.

It will be evident to those skilled in the art that the compounds of the present invention can exist in both racemic and optically active form. In the compounds wherein the hydrogen substituent at the 7-position is trans to the 9a-hydrogen, those compounds having the absolute stereochemical formula

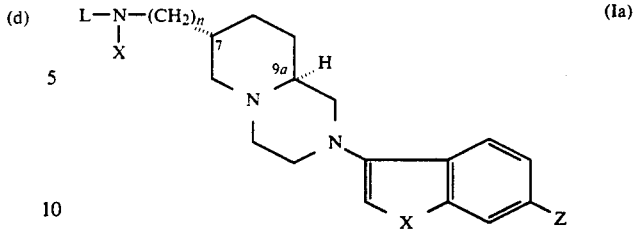

(Ia)

are generally more active than their enantiomers (mirror images). In the formula (Ia), the stereochemical designation, without exception, will be 9aS, while the stereochemical designation at the 7-position will vary, depending on the exact values of n, L and X. However, when n is 2 in the formula (Ia), the latter stereochemical designation will invariably be 7S.

The present invention is further directed to pharmaceutically compositions and to a method of treating psychotic patients with a neuroleptic amount of a compound of the formula (I).

The present invention is also directed to intermediates useful in the synthesis of the compounds of the formula (I), depicted as follows:

(i)

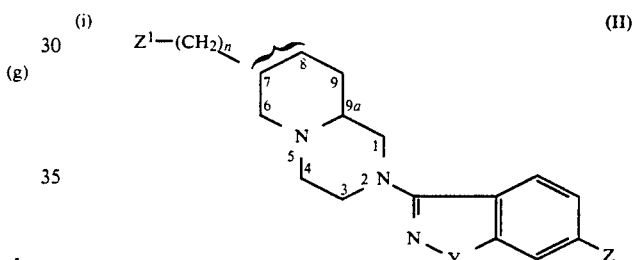

(II)

wherein Z, Y and n are as defined above; and $Z^1$ is NHX, OH, $OSO_2R^5$, $N_3$, CN or

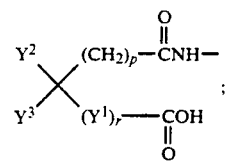

;

X, $Y^1$, $Y^2$, $Y^3$, p and r are as defined above; and $R^5$ is $(C_1-C_3)$alkyl, phenyl or tolyl;
with the proviso that when $Z^1$ is CN, n is other than 4;

(ii)

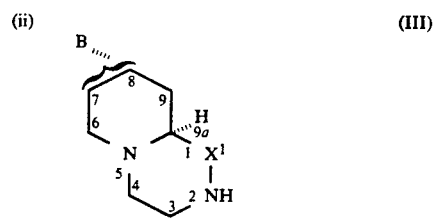

(III)

wherein, in a first alternative, B is $(C_1-C_3)$alkoxy-carbonyl and $X^1$ is C=O; or in a second alternative, $X^1$ is $CH_2$ and B is $HOCH_2$;

(iii)

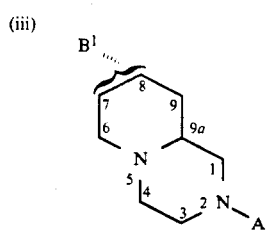

wherein, in the first alternative, A is hydrogen or an amine protecting group removable by catalytic hydrogenation;

B¹ is a group

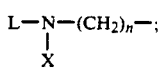

and n, L and X are as defined above;

or, in a second alternative,

A is an amine protecting group removable by catalytic hydrogenation;

B¹ is $Z^1-(CH_2)_n-$; and $Z^1$ and n are as defined above;

(iv)

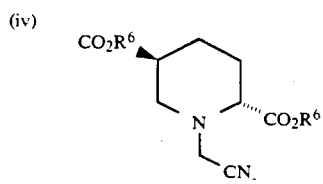

wherein $R^6$ is $(C_1-C_3)$alkyl; and (v)

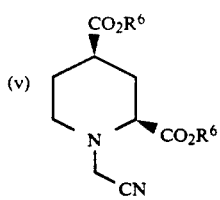

wherein $R^6$ is as defined above.

DETAILED DESCRIPTION OF THE INVENTION

The present invention is readily carried out, there being several processes which are quite general for use in the preparation of the present antipsychotic agents of the formula (I).

A quite generally useful precursor is an amino compound of the formula (VII)

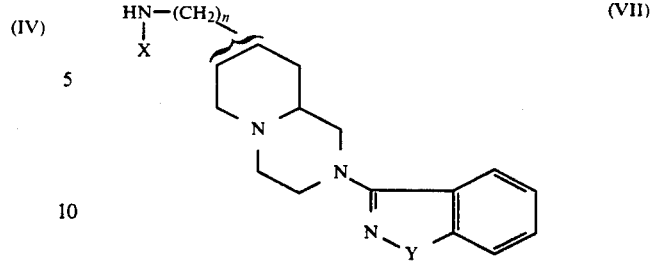

wherein n, X and Y are as defined above. When the derived product of formula (I) has L and X taken separately, this is the preferred method of preparation, since the amine of formula (VII) is readily acylated using an activated form of an acid of formula $R(CH_2)_mCOOH$, e.g., as the acid chloride, the acid anhydride or a classical mixed anhydride formed by interaction of the acid with an alkoxy or phenoxy chloroformate, or activated by a classical peptide bond forming reagent such as dicyclohexylcarbodiimide. When the derived product has L and X taken together, the primary amine of formula (VII), wherein X is necessarily hydrogen, is heated with an excess of a corresponding cyclic anhydride to form a compound wherein L and X are taken together to form a diradical of the above formulas (a), (b), (c) or (d). Alternatively, these cyclic imides are prepared by reaction of substantially one equivalent of cyclic anhydride, generally under more moderate temperature conditions so as to form an intermediate half-amide half-acid which is then cyclized by heating with a more readily available anhydride such as acetic anhydride. When L and X are taken together to form a diradical of the above formulas (e) or (f), the compounds (I) can be similarly prepared from precursors suitably disubstituted with nucleophilic displaceable groups such as chloro, bromo or methansulfonyloxy in the presence of a base which will neutralize the coproduced acid. The conditions appropriate for such nucleophilic displacement reactions are detailed below. When L and X are taken together to form the group of the above formula (g), the compounds (I) can be prepared from the corresponding sulfonic acid appropriately substituted with a nucleophilic displaceable group by two stage nucleophilic displacement followed by cyclization of the resulting amine/sulfonic acid, e.g., by heating in excess acetic anhydride.

The required amino precursors of the formula (a) are prepared according to methods extensively exemplified below. When optically active products are desired, this precursor amine can be resolved via its diastereomeric salts with an optically active acid, as exemplified below.

Further, quite generally useful precursors are those of the formula (VIII)

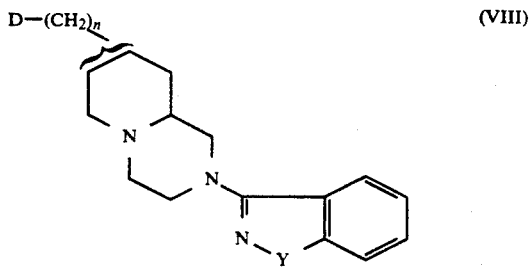

wherein n and Y are as defined above and D is a nucleophilic displaceable group such as chloro, bromo or methanesulfonyloxy. The latter so-called mesylate esters are preferred since they are readily available from the corresponding alcohol, the preparation of which is extensively exemplified below. When the derived product of formula (I) has L and X taken together, this is the preferred method since the required nucleophilic displacing groups are generally readily available. When L and X taken together form an imide or cyclic sulfonamide, the preferred reagents are the anionic derivatives of the corresponding imides, e.g.,

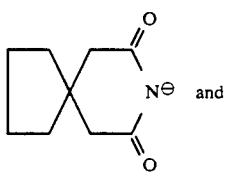

and

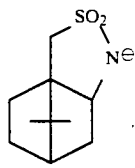

When L and X taken together derive from a simple piperidine derivative, i.e.,

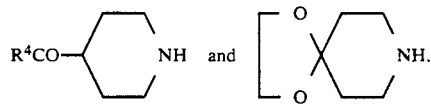

the free amine rather than the corresponding anionic form is generally used. Such nucleophilic displacement reactions are typically carried out with an excess of one of the reagents, in order to force this second order reaction to completion within a reasonable period of time. This will usually be an excess of the most readily available reagent, which in the present case is generally the imide anion or the amine. The reaction is generally carried out in the presence of at least one molar equivalent excess of a base so as to neutralize the molar equivalent of acid produced as a by-product. This can be the amine reagent itself, or more strongly basic, relatively non-nucleophilic base such as triethylamine or 2,6-lutidine. The nucleophilic displacement is generally carried out in a reaction-inert solvent, preferably one which is relatively polar so as to solubilize the reagents and promote more rapid reaction. Temperature is not critical, but will generally be in a range above room temperature so as to promote a reasonably rapid rate of reaction, but not so high as to promote undesired side reactions and degradation.

The alcohols used in the preparative method are readily available from corresponding cis- and trans-piperidine dicarboxylic acid esters, as extensively exemplified below. Such alcohols are potentially resolved by formation of diastereomeric esters with optically active acids. Such esters are generally separable, for example, by conventional chromatographic methods. Once separated, the diastereomeric esters are hydrolyzed to yield the desired optically active alcohol.

A third general method is to react a precursor compound of the formula

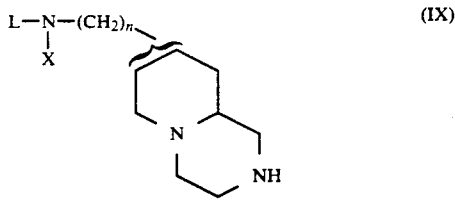

wherein n, L and X are as defined above, with the appropriate 3-chlorobenzo[d]isoxazole/isothiazole derivative of the formula

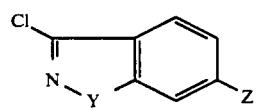

where Y and Z are as defined above. This reaction is carried out under substantially the same nucleophilic displacement conditions which are described above for the reaction of certain piperidine derivatives with the halo or mesylate derivatives of formula (VIII).

Here again, the required starting amine of the formula (IX) is generally prepared according to conventional methods from the corresponding cis or trans-piperidine dicarboxylate diester. Here again, the basic amino compounds of the formula (IX) are suitable substrates for conventional optical resolution in the form of diastereomeric salts formed with an optically active acid.

All clinically effective antipsychotic agents block dopamine binding to D-2 receptors, and demonstrate functional antagonism of dopamine-mediated behaviors in animals. Although the standard antipsychotics interact with a wide variety of neurotransmitter receptors, their potency in blocking D-2 binding is the only activity which shows a highly significant correlation with their oral clinical dosage (Creese et al., Science, 192:481–483, 1976). This clinical effect is believed to result from actions on mesolimbic-mesocortical dopamine projections to the forebrain, specifically inhibition of dopamine hypersensitivity caused by increased receptor density, as demonstrated in post-mortem studies of schizophrenic brains (Lee et al., Nature, 274:897, 1978).

The relative ability of the present compounds of the formula (I) to displace binding at the D-2 receptors was determined according to standard radioligand homogenate binding techniques, as follows. Adult, male Sprague-Dawley rats (3 per assay) were decapitated, the brains quickly removed and caudate-putamen was dissected out. Tissue was homogenized in 50 volumes of ice-cold 50 mM Tris-HCl buffer containing 100 mM NaCl and 1 mM $MgCl_2$ and adjusted to pH 7.2. This mixture was centrifuged twice at $20,000 \times g$ for 15 minutes each, the supernatent being discarded each time and the pellet resuspended in fresh buffer with homogenization. The final pellet was resuspended in buffer to a concentration of 5.6 mg/ml. This tissue suspension was then added to tubes containing a fixed concentration of 3H-spiroperidol (0.2 nM), and various concentrations of test drug. Other tubes contained only buffer ("total") or a saturating concentration of (+)butaclamol (10 $\mu M$ = "blank"). The tubes (final volume—1.0 ml) were incubated at 37° C. for 15 minutes, then rapidly filtered under vacuum through glass fiber filters and rinsed with 12 ml of ice-cold buffer in a Brandel Cell Harvester. The filters were then removed and counted in a scintillation counter using 5 ml of Beckman ReadySafe scintillation fluid. The resulting counts were then used to generate the $IC_{50}$, or extrapolated concentration of test drug necessary to inhibit one-half of the binding, for each compound in question. (Method of Leysen et al., Biochemical Pharmacology, 27:307–316 (1978).

The antipsychotic activity of the present compounds is also demonstrated by their neuroleptic activity using methods based on standard procedures. In one method, adult male Sprague-Dawley rats are pretreated with appropriate doses of the test compound by subcutaneous injection. One half hour later, all rats are injected intraperitoneally with 1 mg/kg apomorphine hydrochloride dissolved in an 0.1% ascorbate solution. The rats are rated behaviorally according to the following stereotypy scale at 5, 15, 25, 35 and 45 minutes after the apomorphin injection: 0=alert but not moving, 1=moving about the cage, 2=discontinuous sniffing behavior, 3=continuous sniffing with discontinuous oral movements, and 4=continuous licking and chewing movements. Compounds with neuroleptic activity will lower the overall stereotypy score of the drug-treated groups, relative to untreated control rats, in proportion to their antagonist potency at the dopamine receptor.

The biological activity of the compounds of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension and social or emotional withdrawal in psychotic patients.

A compound of formula (I), or a pharmaceutically-acceptable salt thereof, is administered to a human subject either alone, or, preferably, in combination with pharmaceutically-acceptable carriers or diluents, in a pharmaceutical composition, according to standard pharmaceutical practice. These compositions are administered orally or parenterally. Parenteral administration includes especially intravenous and intramuscular administration. Additionally, in a pharmaceutical composition comprising a compound of formula (I), or a pharmaceutically-acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of a neuroleptic agent of this invention, the compounds are administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from about 1 to 500 mg, preferably about 5 to 100 mg, in single or divided doses, orally or parenterally. In some instances it may be necessary to use dosages outside these limits.

The following examples are provided solely for the purpose of further illustration. Nomenclature used herein, including designation of relative stereochemistry (R*,S*) and absolute stereochemistry (R,S), is according to Rigaudy et al., IUPAC Nomenclature of Organic Chemistry, 1979 Edition, Pergamon Press, New York.

EXAMPLE 1

Racemic Dimethyl trans-1-(2(Phthalimido)-ethyl)piperidine-2,5-dicarboxylate

To a well-stirred bi-phasic mixture consisting of sodium carbonate (500 g, 4.72 mol) in water (3 liters) and trans-2,5-piperidine dicarboxylate dimethyl ester hydrochloride (280 g, 1.18 mol) in methylene chloride (4.5 liters), a solution of 2-phthalimido-ethyl triflate (417 g, 1.29 mol) in methylene chloride (3 liters) was added in a steady stream over a 3 hour period. The organic layer was separated, and the aqueous layer was extracted with fresh methylene chloride (3 liters). The combined organic extracts were washed with water (3 liters), then with brine (3 liters), dried with anhydrous magnesium sulfate and finally, concentrated in vacuo to a solid. The entire residue was triturated in refluxing ether (3 liters), with vigorous stirring, for 15 minutes. After cooling to ambient temperature, the solution was poured into hexanes (3 liters), and the resulting mixture was stirred for 18 hours. The resulting colorless solid was collected by filtration, and the filter cake was washed with hexanes (1 liter). In vacuo drying afforded 437.3 g (99.1% yield) of the title compound as a colorless solid. TLC Rf (ethyl acetate/methylene chloride=1:1 in volume; iodoplatinate spray): 0.5.

EXAMPLE 2

Racemic Methyl (7R*,9aS*)-4,6,7,8,9,9a-Hexahydro-2H,3H-pyrido[1,2-a]-pyrazin-1-one-7-carboxylate To a well-stirred suspension of the title product of Example 1 (194 g, 0.52 mol) in methanol (3 liters), hydrazine monohydrate (57.1 g, 1.14 mol) was added. The reaction mixture was then stirred for 18 hours at ambient temperature. Methylene chloride (2 liters) was added, and the resulting mixture was vigorously stirred for 1 hour. The resulting white solids were filtered, and the filtercake was washed with methylene chloride (1 liter) before being discarded. In vacuo concentration of the filtrate afforded a colorless solid, which was granulated and then vigorously stirred in refluxing methylene chloride (3 liters) for 10 minutes. The cooled mixture was filtered, and the resulting filtrate was concentrated in vacuo to afford present title compound (89.4 g, 81.6% yield) as an ivory solid. TLC Rf (methylene chloride/methanol=9:1 in volume; iodoplatinate spray): 0.38.

EXAMPLE 3

Racemic
(7R*,9aS*)-Perhydro-7-(hydroxymethyl)-1H-pyrido[1,2-a]pyrazine

To a stirred slurry of the amide-ester title product of Example 2 (244 g, 1.15 mol) in anhydrous tetrahydrofuran (THF, 5.5 liters), a 1.0M solution of lithium aluminum hydride (2.33 liters, 2.33 mol) was added dropwise under nitrogen while maintaining the temperature of the reaction mixture below 40° C. The mixture was then heated at reflux for 18 hours. After cautious dropwise addition of water (90 ml) to the reaction (cooled to ambient temperature) followed by the addition of 15% aqueous sodium hydroxide (90 ml) and finally, more water (270 ml), the mixture was stirred for 1 hour. Insoluble inorganic salts were removed by filtration, and the resulting filtrate was concentrated in vacuo to afford present title compound as a light yellow solid (179.4 g, 90.6% yield), sufficiently pure for use in the next step without further purification. TLC Rf (methylene chloride/methanol/concentrated aqueous ammonia=3:1:0.1 in volume; iodoplatinate spray): 0.19.

EXAMPLE 4

Racemic
(7R*,9aS*)-2-(Benzo[d]isoxazol-3-yl)-perhydro-7-(hydroxymethyl)-1H-pyrido[1,2-a]pyrazine A stirred solution of alcohol-amine title product of Example 3 (179.4 g, 1.05 mol), 3-chloro-1,2-benzo[d]isoxazole (194.2 g, 1.26 mol), and 1,8-diazabicyclo-[5.4.0]undec-7-ene (DBU, 197.9 g, 1.30 mol) in pyridine (400 ml) was heated at 100° C. for 18 hours. After cooling to 35° C., water (3 liters), methylene chloride (2.5 liters) and, finally, saturated aqueous sodium carbonate (2 liters) were added, and the resulting biphasic mixture was vigorously stirred for 3 hours. The tan solid precipitate which formed during the stirring period was filtered, and the filter cake was washed first with water and then with hexane (1 liter of each) prior to being dried in vacuo. Trituration of the entire sample (216 g) with isopropyl alcohol (630 ml) followed by filtration and in vacuo drying afforded present title compound (154.5 g, 51% yield) as a light tan powder, sufficiently pure for use in the next step without further purification. TLC Rf (methylene chloride/methanol=9:1 in volume; iodoplatinate spray): 0.50. $^{13}$CNMR (CDCl$_3$) delta 164.0, 161.1, 129.5, 122.3, 122.1, 116.2, 110.5, 66.3, 60.3, 58.7, 54.3, 53.7, 48.3, 39.1, 29.0, 26.7.

EXAMPLE 5

Racemic
(7R*,9aS*)-2-(Benzo[d]isoxazol-3-yl)-perhydro-7-(methanesulfonyloxymethyl)-1H-pyrido[1,2-a]pyrazine To a chilled (5° C.) and stirred slurry of the alcohol title product of Example 4 (154.0 g, 0.54 mol) and triethylamine (81.76 ml, 59.6 g, 0.589 mol) in methylene chloride (3.0 liters), a solution of methanesulfonyl chloride (43.55 ml, 64.5 g, 0.563 mol) in methylene chloride (350 ml) was added dropwise over 30 minutes. TLC monitoring (methylene chloride/methanol=9:1 in volume; iodoplatinate spray) of the reaction mixture after an additional ½ hour of stirring indicated incomplete reaction. Complete reaction was realized within ½ hour after addition of a second portion of triethylamine (8.23 ml, 6.0 g, 59.3 mmol) and methanesulfonyl chloride [4.32 ml, 6.4 g, 55.9 mmol) added dropwise as a methylene chloride (20 ml) solution]. Water (3 liters) and methylene chloride (1.5 liters) were added, and the biphasic mixture was vigorously stirred prior to separation of the organic and aqueous phases. The aqueous portion was then extracted with a fresh portion of methylene chloride (1.5 liters). The organic extracts were then combined, washed with brine (twice with 2 liter portions) and dried over anhydrous sodium sulfate. Concentration in vacuo afforded the present title compound as a tan solid (178.0 g, 90.2% yield). TLC Rf (methylene chloride/methanol=9:1 in volume; iodoplatinate spray): 0.24. MS m/z 365.1 (M, C$_{17}$H$_{23}$N$_3$O$_4$S). $^{13}$CNMR (CDCl$_3$) delta 164.0, 160.9, 129.6, 122.4, 122.1, 116.0, 110.5, 71.9, 59.9, 57.7, 54.0, 53.3, 48.1, 37.4, 35.9, 28.4, 26.2.

EXAMPLE 6

Racemic
(7S*,9aS*)-2-(Benzo[d]isoxazol-3-yl)-7-(cyanomethyl)-perhydro-1H-pyrido[1,2-a]pyr A stirred solution of the mesylate title product of Example 5 (177.5 g, 0.486 mol) and sodium cyanide (35.7 g, 0.729 mol) in N,N-dimethylformamide (3.0 liters) was heated at 110° C. for 18 hours. The solvent was removed in vacuo, and the resulting tan solid residue was dissolved in a water/methylene chloride (2.5 liters of each) biphasic mixture. The pH of the well-stirred mixture was adjusted to 10 (saturated aqueous sodium carbonate). The layers were then separated, and the aqueous phase was extracted with a fresh portion of methylene chloride (1.5 liters). The combined organic extracts were washed with brine (two 1 liter portions), dried over anhydrous sodium sulfate and concentrated in vacuo to afford present title compound as a tan solid (137.3 g, 95.3% yield). TLC Rf (ethyl acetate/hexane=1:1 in volume; iodoplatinate spray): 0.20. $^{13}$CNMR (CDCl$_3$) delta 164.0, 161.0, 129.6, 122.4, 122.0, 117.9, 116.0, 110.5, 59.9, 59.5, 53.9, 53.3, 48.1, 32.9, 29.6, 28.7, 22.1. In this product, the 7,9a-hydrogens are still trans.

By the same method, the title mesylate product of Example 24 is converted to the corresponding nitrile, racemic (7R*,9aS*)-2-(Benzo[d]isoxazol-3-yl)-7-(3-cyanopropyl)perhydro-1H-pyrido[1,2-a]pyrazine, also having 7 and 9a hydrogen substituents trans.

EXAMPLE 7

Racemic
(7S*,9aS*)-7-(2-Aminoethyl)-2-(benzo[d]isoxazol-3-yl)perhydro-1H-pyrido[1,2-a]pyrazine To a stirred mixture of the nitrile title product of Example 6 (136.9 g, 0.462 mol) in anhydrous tetrahydrofuran (3.5 liters), a 1.0M solution of lithium aluminum hydride (LAH) in tetrahydrofuran (693 ml, 0.693 mol) was added dropwise over a 1 hour period. The reaction was heated at reflux for 6 hours, then stirred for 18 hours at ambient termperature and, finally, quenched by cautious dropwise addition of water/tetrahydrofuran (26 ml and 30 ml respectively), 15 percent aqueous sodium hydroxide (26 ml), and water (80 ml). The mixture was stirred for 0.5 hour. Anhydrous sodium sulfate (400 g) was added, and the inorganic salts were filtered. The filter cake was washed with tetrahydrofuran (800 ml) and methylene chloride (1 liter). The washings were combined with the filtrate, and the resulting solution was concentrated in vacuo to afford the present title compound as a yellow solid (131.9 g, 95% yield). TLC Rf (methylene chloride/methanol/concentrated aqueous ammonia=9:1:0.1 in volume; iodoplatinate spray): 0.28. $^{13}$CNMR (CDCl$_3$) delta 164.0, 161.1, 129.4, 122.2, 122.1, 116.2, 110.4, 61.7, 60.2, 54.2, 53.8, 48.3, 39.7, 38.7, 33.9, 30.7, 29.4.

By the same method the 3-cyanopropyl substituted product of the preceding Example is converted to the corresponding 4-aminobutyl derivative, which in turn is converted to the corresponding imide derivatives by the methods of Examples 10–12.

EXAMPLE 8

Optically Active
(7S,9aS)-7-(2-Aminoethyl)-2-(benzo[d]isoxazol-3-yl)perhydro-1H-pyrido[1,2-a]pyrazine Racemic title amine of Example 7 (131.5 g, 0.438 mol) was dissolved in refluxing ethanol (2.4 liters). S-(+)-mandelic acid (66.6 g, 0.438 mol) was added, affording a clear solution which was allowed to cool slowly and stand at ambient temperature for 18 hours. The colorless crystalline precipitate was filtered, and the cake was washed thrice with 300 ml portions of diethyl ether. In vacuo drying afforded 92.6 g of colorless crystalline (partially resolved) salt; m.p. 205°–210° C. The entire sample was then refluxed in ethanol (1.8 liters) for one hour, affording a solution-suspension which was filtered after being allowed to cool to ambient temperature. Washing of the filter cake with two 300 ml portions of diethyl ether followed by drying in vacuo afforded 75.6 g of colorless crystalline salt; m.p. 214°–217° C., further progressed toward optical resolution and isolation of the 7S,9aS-(−)-enantiomer as its S-(+)-mandelic acid salt. Again, the entire sample was refluxed in ethanol (1.0 liter) for 0.5 hours, cooled to ambient temperature and allowed to stand for 18 hours. Filtration followed by diethyl ether-washing of the filter cake and in vacuo drying afforded 66.3 g of colorless crystals; m.p. 216°–218° C. The just-described crystallization procedure, utilizing 1 liter of ethanol as the crystallization solvent was repeated five more times to afford 45.1 g of resolved S-(+)-mandelic acid salt of the 7S,9aS-(−)-enantiomer; m.p. 223°–224° C. The entire sample was dissolved in a biphasic methylene chloride (2.5 liters)/water (1.4 liters) mixture with the pH adjusted to 9 (saturated aqueous sodium carbonate). The layers were separated, and the aqueous portion was extracted with 2 liters of fresh methylene chloride. Concentration in vacuo of the anhydrous sodium sulfate-dried combined organic extracts afforded present title compound having 7,9a-hydrogen substituents trans (29.9 g, 45.4% yield) as a colorless amorphous solid. $[\alpha]_D^{20}-8.65°$ (c=3.73, methylene chloride). $^{13}$CNMR (CDCl$_3$) delta: identical to that of the racemic amine.

Optical resolution of the racemic (±)-amine to the present 7S,9aS-(−)-amine was confirmed by $^{19}$FNMR comparative studies of its chiral Mosher amide derivative with the corresponding derivative of its 7R,9aR-(+)-counterpart (the product of Example 9). Single crystal X-ray diffraction studies of the latter Mosher amide derivative established the absolute stereo-chemistry of both present and Example 9 title products.

EXAMPLE 9

Optically Active
(7R,9aR)-7-(2-Aminoethyl)-2-(benzo[d]isoxazol-3-yl)perhydro-1H-pyrido[1,2-a]pyrazine A solution of the title racemic amine of Example 7 (1.40 g, 3.79 mmol) and R-(−)-mandelic acid (577 mg, 3.79 mmol) in ethanol (24 ml) was allowed to stand at ambient temperature for 18 hours during which time a heavy crystalline mass formed. The crystalline solid was filtered, washed with diethyl ether and dried in vacuo (270 mg). The entire sample was dissolved in hot ethanol (5 ml). The solution was concentrated in vacuo to a volume of 4 ml and allowed to stand at ambient temperature for 18 hours to complete crystallization. The crystalline mass was filtered, washed with diethyl ether, and dried in vacuo to afford the R-(−)-mandelic acid salt of present title 7R,9aR-(+)-amine, 107 mg (12.5% yield); m.p. 218°–222° C.; $[\alpha]_D^{20}-19.6°$ (C=0.56, methanol).

The entire sample was dissolved in a well-stirred methylene chloride/water (8 ml and 4 ml, respectively) mixture with the pH adjusted to 9.5 (saturated aqueous sodium carbonate). The separated organic extract was washed with an equal volume of water, dried (anhydrous sodium sulfate) and concentrated in vacuo to afford the resolved dextrorotatory amine (51 mg, 7.3% overall yield) as a colorless amorphous solid. TLC Rf (methylene chloride/methanol/concentrated aqueous ammonia=9:1:0.1 in volume; iodoplatinate spray); 0.28; $[\alpha]_D^{20}+7.86°$ (c=1.22, methylene chloride).

EXAMPLE 10

Coupling Method A

Racemic
(7S*,9aS*)-2-(Benzo[d]isoxazol-3-yl)-perhydro-7-(2-(3,3-tetramethyleneglutarimido)-ethyl)-1H-pyrido[1,2-a]pyrazine A mixture consisting of racemic amine title product of Example 7 (465 mg, 1.54 mol) and 3,3-tetramethylene glutaric anhydride (290 mg, 1.70 mmol, Aldrich Chemical Co.) in xylenes (6 ml, boiling range 139°–144° C.) was refluxed vigorously for 18 hours. The xylene solution was carefully decanted from the insoluble tar formed during the reaction period; and the tar was then thoroughly extracted with a fresh portion of xylenes (4 ml). The combined xylene portions were concentrated in vacuo to an oil (0.65 g). Flash chromatography of the entire sample (20 g silica gel, 32–63 mesh; eluting initially with ethyl acetate/hexane=1:1; with decreasing hexane content of the eluting system during the course of the chromatography, leading to pure ethyl acetate elution at its completion) afforded the present title compound (75 mg, 10.8% yield) as a colorless amorphous solid. TLC Rf (ethyl acetate elution, potassium permanganate spray): 0.25.

EXAMPLE 11

Coupling Method B

Racemic
(7S*,9aS*)-2-(Benzo[d]isoxazol-perhydro-7-(2-(3,3-trimethyleneglutarimido)-ethyl)-1H-pyrido[1,2-a]pyrazine A mixture consisting of racemic amine product of Example 7 (98 mg, 0.326 mmol) and 3,3-tetramethylene glutaric anhydride (55 mg, 0.359 mmol) in "xylenes"

(4.0 ml, boiling range 139°-144° C.) was stirred and heated at 150° C. for 15 minutes. The xylene solvent was carefully removed in vacuo (considerable frothing occurs) to afford the crude intermediate non-cyclized, acid-amide as an amber solid. Dehydrative cyclization of the entire sample was carried out in acetic anydride (1.0 ml) by heating the reaction mixture at 100°-110° C. for 2.5 hours. Concentration of the mixture in vacuo afforded a solid residue which was crystallized from isopropanol to afford 48.0 mg (33.7% yield) of the present title compound; m.p. 163.9°-165.3° C. $^{13}$CNMR (CDCl$_3$) delta 171.7, 164.0, 161.0, 129.5, 122.2 (2), 116.0, 110.5, 61.3, 60.2, 54.2, 53.7, 48.2, 44.9, 37.4, 35.1, 34.1, 32.7, 31.1, 30.4, 29.3, 14.7.

EXAMPLE 12

Coupling Method B

Optically Active (7S,9aS)-2-(Benzo[d]isoxazol-3-yl)perhydro-7-(2-(3,3-tetramethyleneglutarimido)ethyl)-1H-pyrido[1,2-a]pyrazine A mixture consisting of 7S-,9aS-(−)-amine title product of Example 8 (1.53 g, 5.09 mmol) and 3,3-tetramethylene glutaric anhydride (0.94 g, 5.59 mmol, Aldrich Chemical Co.) in xylenes (60 ml, boiling range 139°-144° C.) was stirred and heated at 150° C. for 15 minutes. The xylenes were carefully removed in vacuo (considerable frothing occurs) to afford the crude non-cyclized acid-amide as an amber solid [TLC Rf (methylene chloride/methanol=9:1 in volume; iodoplatinate spray): 0.45] sufficiently pure for imide formation without purification. The entire sample was stirred and heated in acetic anhydride (42 ml) at 100°-110° C. for 2.5 hours. The reaction mixture was concentrated in vacuo to afford a solid residue which was partitioned in a well-stirred methylene chloride/water (60 ml and 50 ml, respectively) mixture with the pH adjusted to 9.5 (saturated aqueous sodium carbonate). The phases were separated, and the aqueous phase was extracted with an equal volume of fresh methylene chloride. Concentration in vacuo of the combined organic extracts afforded a yellow solid. Flash chromatography of the entire sample (30 g silica gel, 32-63 mesh; eluting initially with methylene chloride and then adding methanol to increase the polarity of the eluting system to a final methylene chloride/methanol ratio of 97:3 in volume) afforded the pure (TLC inspection in a variety of eluting systems; potassium permanganate spray) title compound as a colorless amorphous solid (1.40 g, 61% yield). $[\alpha]_D^{20}$−4.6° (c=2.3, methylene chloride). TLC Rf (ethyl acetate; potassium permanganate spray): 0.25. HRMS m/z 450.2639 (M, C$_{26}$H$_{34}$O$_3$N$_4$). $^{13}$CNMR (CDCl$_3$) delta 172.1, 164.0, 161.1, 129.5, 122.2 (2), 116.2, 110.5, 61.3, 60.2, 54.2, 53.7, 48.2, 44.9, 39.5, 37.5, 37.4, 34.2, 32.6, 30.4, 29.3, 24.2.

A 230 mg sample of the amorphous product was twice crystallized from isopropanol (2 ml portions), affording 150 mg (65.2% yield) of colorless crystals; m.p. 157°-158° C. The spectroscopic properties and optical rotation of the amorphous and crystalline materials were identical. An enantioselective, quantitative, High Performance Liquid Chromatography (HPLC) assay was developed using a Chiral Type AGP ($\alpha_1$-glycoprotein) column (mobile phase: 0.01M aqueous dihydrogen potassium phosphate/acetonitrile/dimethyloctylamine=900:100:0.2; flow rate: 0.9 ml/minute; ultraviolet HPLC detector at 215 nm wavelength). By this assay, the optical purity of title compound product was found to be ≧95%.

EXAMPLE 13

Mesylate Salt

A 69.6 mg (0.154 mmol) amorphous title product of Example 12 was dissolved in ethyl acetate (1 ml). Methanesulfonic acid (16.6 mg, 0.170 mmol; 98%, Aldrich Chemical Co.) was added, and the resulting solution was stirred for 2 hours at ambient temperature, during which time a heavy crystalline mass formed. The product was filtered, washed with diethyl ether and dried in vacuo to afford the monomesylate salt of the title product of Example 12 as colorless needles, 54 mg (63.9% yield); m.p. 211°-212° C. $[\alpha]^{20}_D$−3.7° (c=2.1, methylene chloride). $^{13}$CNMR (CDCl$_3$) delta 172.5, 164.2, 159.7, 130.2, 123.1, 121.4, 115.3, 110.7, 61.4, 59.6, 52.3, 50.5, 45.7, 44.6, 39.6, 37.5, 36.0, 31.4, 31.1, 28.6, 26.1, 24.2.

The experiment was repeated on a larger scale (468 mg, 1.04 mmol) to afford the identical crystalline product (500 mg) in 88% yield.

The optical purity of this monomesylate salt was determined to be ≧98% by the quantitative enantioselective HPLC assay described in Example 12.

EXAMPLE 14

Optically Active (7R,9aR)-2-(Benzo[d]isoxazol-3-yl)perhydro-7-(2-(3,3-tetramethyleneglutarimido)ethyl)-1H-pyrido[1,2-a]pyrazine By the method of Example 12, dextrorotatory amine product of Example 9 (25 mg, 0.083 mmol) was converted into present title product (15 mg, 40% yield) isolated as a colorless amorphous solid. TLC Rf (ethyl acetate, potassium permanganate spray): 0.25. $[\alpha]_D^{20}$+3.63° (c=0.77, methylene chloride). The optical purity of the title compound was found to be ≧95% by the HPLC enantioselective assay described in Example 12.

EXAMPLE 15

Racemic (7S*,9aS*)-2-(Benzo[d]isoxazol-3-yl)-perhydro-7-(2-(cyclohexylmethylcarbonylamino)-ethyl)-1H-pyrido[1,2-a]pyrazine To a well-stirred solution of cyclohexylacetic acid (35 mg, 0.25 mmol, Aldrich Chemical Co.) in anhydrous methylene chloride (2 ml), 1-hydroxybenzotriazole (37 mg, 0.25 mmol), 1-cyclohexyl-3-(2-morpholinoethyl)carbodiimide metho-p-toluenesulfonate (145 mg, 0.34 mmol, Aldrich Chemical Co.), and amine title product of Example 7 (51 mg, 0.17 mmol) were added, and the resulting mixture was stirred at ambient temperature for 18 hours. The solvent was removed in vacuo, and the residue was partitioned in a well-stirred methylene chloride/water mixture (10 ml of each) with the pH adjusted to 9 (saturated aqueous sodium carbonate). The separated organic phase was concentrated in vacuo to a solid. Flash chromatography of the entire sample (2.0 g silica gel, 32-63 mesh; eluting with methylene chloride/methanol=97:3 in volume) afforded the present title compound as a colorless amorphous solid, 12 mg (17% yield). TLC Rf (methylene chloride/methanol=9:1 in volume, potassium permanganate spray): 0.40; HRMS m/z 424.2854 (M, C$_{25}$H$_{36}$O$_2$N$_4$).

EXAMPLE 16

Racemic (7S*,9aS*)-2-(Benzo[d]isoxazol-3-yl)perhydro-7-(2-(2-thenoylamino)-ethyl)-1H-pyrido[1,2-a]pyrazine A solution consisting of amine title product of Example 7 (100 mg, 0.33 mmol), triethylamine (0.051 ml, 37.2 mg, 0.37 mmol) and 2-thenoyl chloride (0.039 ml, 53.5 mg, 0.37 mmol, Aldrich Chemical Co.) in anhydrous methylene chloride (5.0 ml) was stirred at ambient temperature for 1 hour. An equal volume of water was added, and the pH of the well-stirred mixture was adjusted to 9.5 (aqueous saturated sodium carbonate). The phases were separated, and the aqueous portion was extracted with an equal volume of fresh methylene chloride. The combined organic extracts were washed with water (10 ml), dried (anhydrous sodium sulfate) and concentrated in vacuo to a solid. Flash chromatography of the entire sample (3.8 g silica gel, 32–63 mesh; eluting with ethyl acetate) afforded the title compound as a colorless amorphous solid, 16.8 mg (12.3% yield). TLC Rf (methylene chloride/methanol=9:1 in volume; potassium permanganate spray): 0.51. HRMS 410.1759 corresponding to mass ion $C_{22}H_{26}N_4O_2S$.

EXAMPLE 17

Racemic (7R*,9aS*)-2-(Benzo[d]isoxazol-3-yl)-perhydro-7-((3,3-tetramethyleneglutarimido)-methyl)-1H-pyrido[1,2-a]pyrazine 3,3-Tetramethyleneglutarimide (18.3 mg, 0.11 mmol) was added to a well-stirred suspension of sodium hydride (4.4 mg of 60% sodium hydride mineral oil dispersion; 2.64 mg, 0.11 mmol of sodium hydride) in anhydrous N,N-dimethylformamide (DMF, 0.5 ml). The reaction was stirred and heated to 60° C. under dry nitrogen for 20 minutes. A solution of mesylate title product of Example 5 (20 mg, 0.55 mmol) in anhydrous DMF (1.0 ml) was added and the resulting mixture was stirred at 100° C. for 6 hours. The solvent was removed in vacuo, and the residue was partitioned in a well-stirred methylene chloride/water mixture (15 ml of each) with the pH adjusted to 10 (saturated aqueous sodium carbonate). The organic phase was separated, treated with activated charcoal and filtered, dried (anhydrous sodium sulfate) and, finally, concentrated in vacuo to a colorless amorphous solid. Crystallization of the entire sample from isopropanol afforded 13.2 mg (55% yield) of the present title compound; m.p. 208°–209° C. HRMS 436.2466 corresponding to mass ion $C_{25}H_{32}N_4O_3$.

EXAMPLE 18

Racemic (7R*,9aS*)-7-(Azidomethyl)-2-(benzo[d]isoxazol-3-yl)perhydro-1H-pyrido[1,2-a]pyrazine A mixture consisting of mesylate title product of Example 5 (473 mg, 1.29 mmol) and sodium azide (170 mg, 2.58 mmol) in anhydrous N,N-dimethylformamide (5.0 ml) was stirred at 100° C. for 17 hours. The heterogeneous reaction mixture was concentrated in vacuo to an oily residue which was then partitioned into a well-stirred methylene chloride/water mixture (20 ml of each) with the pH adjusted to 11.5 (saturated aqueous sodium carbonate). The organic phase was separated, dried over anhydrous sodium sulfate and concentrated in vacuo to afford present title product (in which the 7- and 9a-hydrogen atoms are trans) as a light yellow amorphous solid (370 mg, 91.2% yield). TLC Rf (ethyl acetate/methanol/concentrated aqueous ammonia=9:2:0.2 in volume; potassium permanganate spray): 0.78.

By the same method, the 8R*,9aS*)-8-(methanesulfonyloxymethyl) title product of Example 39 is converted to the corresponding (8R*,9aS*)-8-(aminomethyl) derivative in which the 8- and 9a- hydrogen atoms are cis.

EXAMPLE 19

Racemic (7S*,9aS*)-7-(Aminomethyl)-2-(benzo[d]isoxazol-3-yl)perhydro-1H-pyrido[1,2-a]pyrazine A solution of azide title product of Example 18 in an ethanol/methanol mixture (2 ml and 1 ml, respectively) was hydrogenated on a Parr apparatus (50 psi, 26 mg of 5% palladium-on-carbon catalyst) for 2.5 hours. The catalyst was filtered under nitrogen, and the resulting filtrate was concentrated in vacuo to afford present title product as a colorless amorphous solid (50 mg, 99% yield). TLC Rf (ethyl acetate/methanol/concentrated aqueous ammonia=9:2:0.2 in volume, potassium permanganate spray): 0.15. $^{13}$CNMR (CDCl$_3$) delta 164.0, 161.0, 129.5, 122.3, 122.2, 116.1, 110.4, 60.3, 59.6, 54.2, 53.7, 48.2, 46.4, 39.6, 29.0, 28.2.

By the same method, the corresponding 8-(azidomethyl) derivative is converted to the corresponding 8-(aminomethyl) derivative.

EXAMPLE 20

Racemic (7R*,9aS*)-2-(Benzo[d]isoxazol-3-yl)-perhydro-7-((3,3-tetramethyleneglutarimido)-methyl)-1H-pyrido[1,2-a]pyrazine A mixture consisting of amine title product of Example 19 (31 mg, 0.11 mmol) and 3,3-tetramethylene glutaric anhydride (20 mg, 0.12 mmol, Aldrich Chemical Co.) in xylenes (1.0 ml, boiling range 139°-144° C.) was stirred and heated at 105° C. for 10 minutes. After cooling to ambient temperature, the xylenes were carefully removed in vacuo (considerable frothing occurs) to afford the uncyclized acid-amide intermediate as a colorless solid [TLC Rf (methylene chloride/methanol=9:1 in volume; potassium permanganate spray): 0.39], which was used for imide formation without purification. The entire sample was stirred and heated at 105° C. in acetic anhydride (2.0 ml) for 3 hours. The excess acetic anhydride was removed in vacuo to afford a solid residue which was then partitioned in a well-stirred methylene chloride/water (10 ml and 5 ml, respectively) mixture with the pH adjusted to 9 (saturated aqueous sodium carbonate). The organic phase was dried (anhydrous sodium sulfate) and concentrated in vacuo to a solid (33 mg). Flash chromatography of the entire sample (550 mg of silica gel, 32–63 mesh; eluting initially with methylene chloride and then increasing the polarity of the eluting system by adding methanol to a final methylene chloride/methanol ratio of 98:2 in volume) afforded the title compound as a colorless amorphous solid (16.4 mg, 34.8% yield). TLC Rf (methylene chloride/methanol=9:1 in volume; potassium permanganate spray): 0.42. HRMS m/z 436.2466 (M, $C_{25}H_{32}O_3N_4$). $^{13}$CNMR (CDCl$_3$) delta 172.4, 164.0, 161.1, 129.5, 122.2, 122.1, 116.2, 110.5, 60.0, 59.6, 54.3, 53.7, 48.2, 44.9, 42.8, 39.4, 37.7, 35.9, 29.1, 28.4, 24.3.

A sample of the pure amorphous product readily crystallized from isopropanol (m.p. 208°–209° C.). The crystalline product was identical in all respects to that prepared by the method of Example 17.

EXAMPLE 21

Racemic (7S*,9aS*)-7-(Cyclohexylmethylcarbonylaminomethyl)-2-(benzo[d]isoxazol-3-yl)perhydro-1H-pyrido[1,2-a]pyrazine To a well-stirred solution of cyclohexylacetic acid (23 mg, 0.16 mmol. Aldrich Chemical Co.) in anhydrous methylene chloride (1 ml), 1-hydroxybenzotriazole (25 mg, 0.16 mmol), 1-cyclohexyl-3-(2-morpholinoethyl)carbodimide metho-p-toluenesulfonate (100 mg, 0.25 mmol), and amine title product of Example 19 (36 mg, 0.13 mmol) were added. The resulting mixture was stirred at ambient temperature for 18 hours. The solvent was removed in vacuo, and the residue was partitioned in a well-stirred methylene chloride/water mixture (10 ml of each) with the pH adjusted to 9 (saturated aqueous sodium carbonate). The separated organic phase was concentrated in vacuo to a solid. Flash chromatography of the entire sample (2.0 g silica gel, 32–63 mesh; eluting with ethyl acetate:-methanol=9:1 in volume) afforded the present title compound as a colorless amorphous solid, 10 mg (19.5% yield). TLC Rf (methylene chloride/methanol=9:1 in volume; potassium permanganate spray): 0.43. HRMS 410.2684 corresponding to mass ion $C_{24}H_{34}N_4O_2$.

EXAMPLE 22

Racemic (7S*,9aS*)-2-(Benzo[d]isoxazol-3-yl)-7-(4-(4-fluorobenzoyl)piperidinomethyl)-perhydro-1H-pyrido[1,2-a]pyrazine To a solution of 4-(p-fluorobenzoyl)piperidine (11.9 mg, 0.058 mmol) in methylisobutylketone (0.2 ml), sodium carbonate (15.2 mg, 0.14 mmol), potassium iodide (1 mg), and a solution of mesylate title product of Example 5 (21 mg, 0.058 mmol) in methylisobutylketone (0.3 ml) were added, and the resulting mixture was refluxed for 4 hours. The solvent was removed in vacuo, and the residue was dissolved in a well-stirred methylene chloride/water (20 ml and 10 ml, respectively) mixture (pH 11). The phases were separated, and the aqueous portion was extracted twice with 25 ml of fresh methylene chloride. The combined organic extracts were treated with activated charcoal, dried (anhydrous sodium sulfate) and concentrated in vacuo to a colorless solid. Crystallization of the entire sample from isopropanol afforded present title compound, 13.9 mg, 56.7% yield; m.p. 179°–181° C. TLC Rf (ethyl acetate/-methanol=9:1 in volume; potassium permanganate spray): 0.17.

EXAMPLE 23

Racemic (7S*,9aS*)-2-(Benzo[d]isoxazol-3-yl)perhydro-7-(2,2-di(methoxycarbonyl)-ethyl)-1H-pyrido[1,2-a]pyrazine To a solution of dimethyl malonate (2.054 g, 15.5 mmol) in anhydrous N,N-dimethylformamide (80 ml), sodium hydride (0.77 g of 60% sodium hydride in mineral oil dispersion; 462 mg, 19.3 mmol sodium hydride) was added, and the stirred mixture was heated at 55° C. for 1 hour. Mesylate title product of Example 5 (5.44 g, 14.9 mmol) was added, and the resulting mixture was stirred and heated at 100° C. for 42 hours. The solvent was removed in vacuo leaving a solid residue which was then dissolved in a well-stirred methylene chloride/saturated aqueous bicarbonate biphasic mixture (150 ml of each; pH=8.9). The organic phase was separated, washed successively with equal volumes of water and brine, dried (anhydrous sodium sulfate) and concentrated in vacuo to a solid. The entire sample was taken up in warm ethyl acetate. Hexane was then added until the solution became turbid. Within 3 hours standing at ambient temperature, present title product crystallized (2.60 g, 43.5% yield; m.p. 134°–138° C.). TLC Rf (ethyl acetate, potassium permanganate spray): 0.36.

EXAMPLE 24

Racemic (7S*,9aS*)-2-(Benzo[d]isoxazol-3-yl)perhydro-7-(3-(methanesulfonyloxy)-propyl)-1H-pyrido[1,2-a]pyrazine Title dimethylmalonate derivative of Example 23 (0.65 g, 1.62 mmol) was vigorously refluxed in concentrated hydrochloric acid for 3 hours. The pH of the reaction mixture (cooled to ambient temperature) was adjusted to 6.8 by dropwise addition of 10% aqueous lithium hydroxide. Concentration of the mixture in vacuo afforded the intermediate, solid, crude lithium salt of racemic (7S*,9aS*)-7-(2-carboxyethyl)perhydro-2-(benzo[d]isoxazol-3-yl)-1H-pyrido[1,2-a]pyrazine.

The entire sample was stirred for 18 hours in methanol-concentrated sulfuric acid (7.0 and 0.12 ml, respectively). Concentration in vacuo afforded an oily residue which was dissolved in a ethyl acetate/saturated aqueous sodium bicarbonate (25 ml of each; pH=7.8) biphasic mixture. The organic phase was separated and concentrated in vacuo to an oil (0.48 g). Flash chromatography of the entire sample (25 g of silica gel, 32–63 mesh, elution initially with methylene chloride and finally with methylene chloride/methanol=97:3 in volume) afforded the corresponding pure methyl ester (0.23 g, 41.8% yield) as a colorless oil. TLC Rf (ethyl acetate, potassium permanganate spray): 0.20. $^{13}$CNMR (CDCl$_3$) delta 174.0, 164.0, 161.0, 129.5, 122.3, 122.1, 116.1, 110.5, 61.3, 60.2, 54.1, 53.7, 51.6, 48.2, 35.6, 31.5, 30.2, 29.5, 29.2.

A reaction mixture consisting of this methyl ester (23 mg, 0.07 mmol) and lithium aluminum hydride (0.167 ml of a 1.0M solution in tetrahydrofuran; 0.17 mmol of lithium aluminum hydride) in anhydrous tetrahydrofuran (0.5 ml) was refluxed for 4 hours. The reaction was cooled to ambient temperature and quenched with a methanol (7 drops) and tetrahydrofuran (5 ml) solution. The inorganics were filtered, and the filtrate was concentrated in vacuo to afford the corresponding alcohol product, racemic (7S*,9aS*)-2-(benzo[d]isoxazol-3-yl)-perhydro-7-(3-hydroxypropyl)-1H-pyrido[1,2-a]pyrazine, as a colorless amorphous solid (15.9 mg, 75.4% yield). TLC Rf (methylene chloride/methanol=9:1 in volume, potassium permanganate spray): 0.35. $^{13}$CNMR (CD$_3$OD) delta 165.1, 162.2, 131.2, 123.8, 123.7, 116.9, 111.0, 63.0, 62.5, 61.7, 55.0, 54.3, 48.9, 36.7, 31.6, 31.4, 30.6, 29.9.

By the method of Example 5, this alcohol (20 mg, 0.06 mmol) was converted to present title mesylate ester, isolated as an amorphous solid in quantitative yield. TLC Rf (ethyl acetate, potassium permanganate spray): 0.17.

EXAMPLE 25

Racemic
(7R*,9aS*)-2-(6-Chlorobenzo[d]-isoxazol-3-yl)perhydro-7-(hydroxymethyl)-1H-pyrido[1,2-a]pyrazine By the method of Example 4, the alcohol-amine title product of Example 3 (203 mg, 1.19 mmol) and 3,6-dichlorobenzo[d]isoxazole were converted into present title product (206 mg, 53.8% yield) isolated as a pale yellow amorphous solid. In this product the 7and 9a-hydrogen substitutents remain trans. TLC Rf (methylene chloride/methanol=9:1 in volume; potassium permanganate spray): 0.41. $^{13}$CNMR (CDCl$_3$) delta 164.2, 160.6, 136.1, 123.3, 122.8, 114.9, 110.8, 65.9, 60.2, 58.7, 54.1, 53.4, 48.0, 39.0, 28.8, 26.7.

EXAMPLE 26

Racemic
(7R*,9aS*)-2-(6-Chlorobenzo[d]isoxazol-3-yl)perhydro-7-((3,3-tetramethyleneglutarimido)methyl)-1H-pyrido[1,2-a]pyrazine By the methods of Examples 5 and 17, the alcohol title product of Example 25 (66 mg, 0.165 mmol) was converted to present title product (13.7 mg, 17.6% yield) and isolated as a colorless solid. TLC Rf (methylene chloride/methanol=9:1 in volume; potassium permanganate spray): 0.64. $^{13}$CNMR (CDCl$_3$) delta 172 4, 164.4, 160.9, 136.0, 123.2, 122.7, 115.1, 110.8, 59.9, 59.5, 54.2, 53.6, 48.2, 44.9, 42.8, 39.4, 37.7, 35.9, 29.0, 28.3, 24.3.

EXAMPLE 27

Racemic
(7S*,9aS*)-2-(6-Chlorobenzo[d]isoxazol-3-yl)-perhydro-7-(hydroxymethyl)-1H-pyrido[1-2a]pyrazine By the method of Example 4, racemic (7S*,9aS*)-7-(hydroxymethyl)perhydro-1H-pyrido[1,2-a]pyrazine (300 mg, 1.76 mmol; also called cis-7-hydroxymethyl-2,3,4,6,7,8,9,9a-octahydro-1H-pyrido[1,2-a]pyrazine, prepared from dimethyl cis-piperidine-2,5-dicarboxylate according to the methods of Preparations 1–5 of published International patent application, International Publication No. WO 90/08144) and 6-chlorobenzo[d]isoxazole were converted to present title product (369 mg, 65% yield) and isolated as a colorless solid. In this product the hydrogen atoms substituted at the 7- and 9a-positions are cis, as indicated by the specified 7S*,9aS*-stereochemistry. TLC Rf (methylene chloride/methanol=9:1 in volume; potassium permanganate spray): 0.30. $^{13}$CNMR (CDCl$_3$) delta 164.3, 160.6, 136.1, 123.3, 122.7, 114.9, 110.8, 67.6, 60.1, 58.2, 54.1, 53.6, 48.3, 34.4, 26.9, 26.3.

EXAMPLE 28

Racemic
(7S*,9aS*)-2-(6-Chlorobenzo[d]isoxazol-3-yl)perhydro-7-((3,3-tetramethyleneglutarimido)methyl)-1H-pyrido[1,2-a]pyrazine By the methods of Examples 5 and 17, the title alcohol product of Example 27 (13.8 mg, 0.04 mmol) was converted to present title product (20 mg, 100% yield), isolated as a colorless foam. TLC Rf (methylene chloride/methanol=9:1 in volume; potassium permanganate spray): 0.73. $^{13}$CNMR (CDCl$_3$) delta 172.5, 164.4, 160.8, 136.0, 123.1, 122.8, 115.1, 110.8, 60.4, 58.5, 54.1, 53.6, 48.2, 45.1, 41.5, 39.4, 37.6, 32.9, 25.0, 24.8, 24.3.

EXAMPLE 29

Racemic
(7R*,9aS*)-2-(Benzo[d]isothiazol-3-yl)-perhydro-7-(hydroxymethyl)-1H-pyrido[1,2-a]pyrazine A mixture consisting of the mixed title products of Preparation 4 below (230 mg, 1.38 mmol), 3-chloro-1,2-benzisothiazole (460 mg, 2.78 mmol), sodium carbonate (280 mg, 2.78 mmol) and potassium iodide (20 mg) in isoamyl alcohol (5.0 ml) was heated at reflux for 18 hours. The reaction mixture was filtered, and the filtrate was concentrated in vacuo to an oil. Flash chromatography of the entire sample (20 g silica gel; 32–64 mesh, eluting with ethyl acetate/methanol=15.2 in volume) afforded 49 mg (17%) of the present title product (derived from the trans-piperidine-2,5-dicarboxylate ester and so having the 7- and 9a-hydrogen substituents trans) as an amorphous solid. TLC Rf (methylene chloride/methanol=9:1 in volume; potassium permanganate spray): 0.28. MS m/z 365.1 (M, $C_{17}H_{23}N_3O_4S$). $^{13}$CNMR (CDCl$_3$) delta 141.8, 133.0, 132.0, 127.8, 126.7, 116.8, 110.0, 66.0, 61.8, 61.6, 58.4, 55.9, 55.6, 39.0, 28.8, 26.6.

EXAMPLE 30

Racemic
(7S*,9aS*)-2-(Benzo[d]isothiazol-3-yl)-perhydro-7-(pyrdroxymethyl-1H-pyrido[1,2-a]pyrazine A mixture of racemic (7S*,9aS*)-7-(hydroxymethyl)-perhydro-1H-pyridopyrazine [also called cis-7-(hydroxymethyl)perhydro-1H-pyrido[1,2-a]pyrazine] prepared according to Preparation 5 at page 28 of above cited WO 90/08144 (1.62 g, 9.56 mmol), 3-chloro-1,2-benzisothiazole (1.47 g, 8.69 mmol), sodium carbonate (2.20 g, 19 mmol) and isoamyl alcohol (8.0 ml) was heated at reflux for 18 hours. Methylene chloride (100 ml) was added, and the mixture was filtered. The filtrate was concentrated in vacuo to an oil. Flash chromatography of the entire sample (30 g silica gel, 32–64 mesh, eluting initially with ethyl acetate and finally with ethyl acetate/methanol=9:1 in volume) afforded present title compound (700 mg, 26.6% yield) as an amorphous solid. TLC Rf (methylene chloride/methanol=9:1 in volume; potassium permanganate spray): 0.34. $^{13}$CNMR (CDCl$_3$) delta 142.9, 133.5, 132.8, 127.8, 126.7, 116.7, 109.8, 65.6, 61.8, 61.6, 57.1, 56.0, 55.6, 34.7, 25.9, 25.8.

EXAMPLE 31

Racemic
(7R*,9aS*)-2-(Benzyloxycarbonyl)-perhydro-7-(hydroxymethyl)-1H-pyrido[1-2a]pyrazine To a solution of the title product of Example 3 (640 mg, 3.76 mmol) in acetone/water (6.3 ml and 2.2 ml, respectively), a solution of benzylchloroformate (0.61 ml, 729 mg, 4.27 mmol) in acetone (2.0 ml) was added dropwise over several minutes while maintaining the pH of the mixture at 9.5 by intermittent dropwise addition of saturated aqueous sodium carbonate. After completing the addition, the reaction was stirred for 5 minutes at ambient temperature. The acetone solvent was removed in vacuo, ethyl acetate (60 ml) and water (30 ml) were added, and the pH of the well-stirred mixture was adjusted to 9.5 (sodium carbonate). The separated organic phase was dried (anhydrous sodium sulfate) and concentrated in vacuo to an oil (940 mg). Flash chromatography of the entire sample [10 g, silica gel, 32–63 mesh, eluting initially with ethyl acetate (100 mg), followed by ethyl acetate/methanol (100 ml, 97:3 in volume) and finally ethyl acetate/methanol (200 ml, 90:10 in volume)] afforded the present title compound as a colorless oil, 350 mg (30.6% yield). TLC Rf (ethyl acetate/methanol/concentrated aqueous ammonia = 9:2:0.2 in volume): 0.63.

EXAMPLE 32

Racemic
(7R*,9aS*)-2-(Benzyloxycarbonyl)-perhydro-7-((3,3-tetramethyleneglutarimido)-methyl-1H-pyrido[1,2-a]pyrazine To a chilled (5° C.) and stirred solution of N-carbobenzyloxy protected intermediate of Example 31 (328 mg, 1.07 mmol) and triethylamine (0.164 ml, 1.18 mmol) in methylene chloride (7 ml), a solution of methanesulfonyl chloride (0.087 ml, 1.13 mmol) was added dropwise. The reaction mixture was stirred at ambient temperature for 15 minutes. Methylene chloride (10 ml) and water (15 ml) were added, and the pH of the well-stirred mixture was adjusted to 9.5 (1N aqueous sodium hydroxide). The organic phase was separated, washed with three equal volumes of water, dried (anhydrous sodium sulfate) and concentrated in vacuo to afford the crude mesylate ester intermediate. The entire sample was dissolved in anhydrous N,N-dimethylformamide (DMF, 2.0 ml), and the resulting solution was added to a DMF (3.0 ml) solution of sodium 3,3-tetramethylene glutarimide prepared from sodium hydride (47 mg of 60% sodium hydride in mineral oil dispersion, 28.2 mg, 1.18 mmol of sodium hydride) and 3,3-tetramethylene glutarimide (198 mg, 1.18 mmol, Aldrich Chemical Co.). The mixture was stirred and heated at 90° C. for 19 hours. Concentration in vacuo afforded an oil, which was dissolved in a well-stirred ethyl acetate/water mixture (30 ml of each) with the pH adjusted to 2.0 (6N concentrated hydrochloric acid). The phases were separated, and the aqueous extract was stirred with a fresh equal volume portion of ethyl acetate with pH adjusted to 8.5 (saturated aqueous sodium carbonate). The separated organic phase was concentrated in vacuo to an oil. NMR inspection showed the desired product contaminated with residual 3,3-tetramethylene glutarimide which was removed by an additional basic work-up (methylene chloride/water, 30 ml of each, with pH adjusted to 9.0 with sodium carbonate). In vacuo concentration of the anhydrous sodium sulfate-dried organic extract afforded present title compound as a colorless viscous oil, 230 mg (47.9% yield). TLC Rf (methylene chloride/methanol = 9:1; potassium permanganate spray): 0.60.

EXAMPLE 33

Racemic
(7R*,9aS*)-7-((3,3-tetramethyleneglutarimido)methyl)-perhydro-1H-pyrido[1,2-a]pyrazine A solution of the title product of Example 32 (230 mg, 0.51 mmol) in a ethanol/methanol mixture (10 ml and 2 ml, respectively) was hydrogenated on a Parr apparatus (50 psig hydrogen pressure over 110 mg of 20% palladium hydroxide-on-carbon catalyst) for 2 hours. The catalyst was filtered under nitrogen, and the resulting filtrate was concentrated in vacuo to afford present title compound as a colorless viscous oil, 150 mg (92% yield).

EXAMPLE 34

Racemic
(7R*,9aS*)-2-(Benzo[d]isothiazol-3-yl)-perhydro-7-((3,3-tetramethyleneglutarimido)-methyl-1H-pyrido[1,2-a]pyrazine A mixture consisting of the title product of Example 33 (90 mg, 0.28 mmol), 3-chloro-1,2-benzisothiazole (95.2 mg, 0.56 mmol) and sodium carbonate (60 mg, 0.56 mmol) in isoamyl alcohol (1.0 ml) was stirred and heated at 110° C. for 1 hour. The mixture was cooled to 50° C. and additional 3-chlorobenzisothiazole (95.2 mg, 0.56 mmol) was added. The reaction was then stirred and heated at 120° C. for three hours. After cooling to ambient temperature, methylene chloride (10 ml) was added, the resulting mixture was filtered, and the filtrate was concentrated in vacuo to an oil. Flash chromatography of the entire sample (3 g silica gel, 32–63 mesh, eluting initially with ethyl acetate/hexane, then with ethyl acetate, and finally with ethyl acetate/methanol/concentrated aqueous ammonia = 9:2:0.1 in volume) afforded the present title compound as a colorless amorphous solid, 25 mg (19.7% yield). TLC Rf (ethyl acetate/hexane = 1:1 in volume): 0.18.

EXAMPLE 35

Racemic Dimethyl
cis-1-(cyanomethyl)-piperidine-2,4-dicarboxylate

A mixture consisting of title product of Preparation 5 dicarboxylic acid dimethyl ester (12.4 g, 61.6 mmol), bromoacetonitrile (5.15 ml, 8.87 g, 73.9 mmol), anhydrous sodium carbonate (26 g, 0.25 mol) and potassium iodide (1.73 g, 10.4 mol) in methylisobutylketone (283 ml) was stirred and refluxed for 18 hours. The reaction was filtered, the solvent was removed in vacuo, and the residue was dissolved in a well-stirred methylene chloride/ water mixture (200 ml and 100 ml, respectively). The layers were separated, and the aqueous portion was extracted twice with 100 ml of fresh methylene chloride. The organic extracts were combined, dried (anhydrous sodium sulfate) and concentrated in vacuo to afford the title compound as a viscous oil in quantitative yield (14.8 g). TLC Rf (methylene chloride/methanol = 9:1 in volume; potassium permanganate spray): 0.78. $^{13}$CNMR (CDCl$_3$) delta 173.7, 171.8, 114.1, 62.1, 52.4, 51.9, 51.5, 43.3, 39.8, 31.7, 27.4.

EXAMPLE 36

Racemic Methyl
(8R*,9aS*)-4,6,7,8,9,9a-Hexahydro-2H,3H-pyrido[1,2-a]-pyrazin-1-one-8-carboxylate A solution of the title product of Example 35 (14.80 g, 61.6 mmol) in methanol/ethyl acetate (250 ml and 100 ml, respectively) was hydrogenated on a Parr apparatus (50 psig hydrogen pressure, 25.2 g of Raneynickel catalyst) for 18 hours at ambient temperature. The catalyst was filtered, and the filtrate was concentrated in vacuo to an amorphous solid. Crystallization of the entire sample from isopropyl alcohol afforded the title compound 5.21 g, 39.9% yield as a colorless crystalline solid, m.p. 185°-186° C. TLC Rf (methylene chloride/methanol = 9:1 in volume; potassium permanganate spray): 0.3. $^{13}$CNMR (CDCl$_3$) delta 174.8, 170.6, 64.2, 54.8, 51.7, 50.8, 41.6, 40.9, 29.7, 27.6.

EXAMPLE 37

Racemic (8R*,9aS*)-8-(Hydroxymethyl)-perhydro-1H-pyrido[1,2-a]pyrazine

By the method of Example 3, the ester-amide title product of Example 36 (5.21 g, 24.6 mmol) was reduced to afford present title alcohol-amine (3.33 g, 81% yield) isolated as a colorless amorphous solid. TLC Rf (ethyl acetate/methanol/concentrated aqueous ammonia = 1:1:0.15 in volume; potassium permanganate spray): 0.24. $^{13}$CNMR (CDCl$_3$) delta 67.8, 60.4, 54.8, 54.7, 51.3, 38.3, 32.8, 30.3, 28.5.

EXAMPLE 38

Racemic (8R*,9aS*)-2-(Benzo[d]isoxazol-3-yl)-perhydro-8-(hydroxymethyl)-1H-pyrido[1,2-a]pyrazine A mixture consisting of alcohol-amine title product of Example 37 (20.0 g, 117 mmol), 3-chloro-1,2-benzisoxazole (36.1 g, 235 mmol) and 1,8-diazabicyclo[5.4.0]-undec-7-ene (DBU, 25.4 g, 25 ml, 167 mmol) in 2,6-lutidine (19.6 ml) was stirred and heated at 140° C. for 18 hours. More DBU (25.4 g, 25 ml, 167 mmol) and 2,6-lutidine (20 ml) were added, and the reaction was stirred at 140° C. for an additional 7 hours. The solvent was removed in vacuo, and the residue was extracted with a well-stirred methylene chloride/water mixture (200 ml of each). The separated aqueous portion was extracted twice with 50 ml of fresh methylene chloride. The combined organic extracts were washed three times with equal volumes of water, dried (anhydrous sodium sulfate) and concentrated in vacuo to a solid. Flash chromatography of the entire sample (414 g, silica gel, 32-63 mesh, eluting with methylene chloride/methanol = 9:1 in volume) afforded the title compound (in which the 8- and 9a-hydrogen substituents are cis) as a colorless amorphous solid, 15.7 g, 46.7% yield. TLC Rf (ethyl acetate/methanol = 15:2 in volume; potassium permanganate spray): 0.18. $^{13}$CNMR (CDCl$_3$) delta 163.9, 160.9, 129.6, 122.3, 122.2, 116.0, 110.4, 67.3, 59.6, 55.0, 53.7, 53.6, 48.1, 38.1, 32.5, 28.4.

EXAMPLE 39

Racemic (8R*,9aS*)-2-(Benzo[d]isoxazol-3-yl)perhydro-8-(methanesulfonyloxymethyl)-1H-pyrido[1,2-a]pyrazine By the method of Example 5 the N-benzisoxazole substituted alcohol of Example 38 (15.7 g, 5.46 mmol) was converted into the corresponding mesylate title product (19 g, 95% yield), isolated as a pale yellow amorphous solid. TLC Rf (methylene chloride/methanol = 9:1 in volume; potassium permanganate spray): 0.53. $^{13}$CNMR (CDCl$_3$) delta 163.8, 160.9, 129.5, 122.3, 122.1, 115.9, 110.3, 73.6, 58.9, 54.3, 53.7, 53.6, 48.2, 37.2, 35.3, 31.9, 28.0.

EXAMPLE 40

Racemic (8R*,9aS*)-2-(Benzo[d]isoxazol-3-yl)-8-(cyanomethyl)-perhydro-1H-pyrido[1,2-a]pyrazine A mixture consisting of mesylate title product of Example 39 (2.0 g, 5.47 mmol) and sodium cyanide (805 mg, 16.4 mmol) in N,N-dimethylformamide (32 ml) was stirred and heated at 100° C. for 18 hours. The solvent was removed in vacuo, and the residue was dissolved in a well-stirred methylene chloride/water mixture (150 ml of each) with the pH adjusted to 9.5 (6N aqueous sodium hydroxide). The layers were separated, and the aqueous portion extracted twice with 100 ml of fresh methylene chloride. The combined organic extracts were dried (anhydrous sodium sulfate) and concentrated in vacuo to a yellow solid (1.53 g). Crystallization of the entire sample from isopropanol/methylene chloride afforded the pure title compound 707 mg, 43.6% yield; m.p. 164°-166° C. $^{13}$CNMR (CDCl$_3$) delta 164.0, 160.9, 129.6, 122.4, 122.1, 118.2, 116.0, 110.5, 59.1, 54.6, 53.6, 53.5, 48.3, 35.1, 32.8, 31.3, 24.2.

EXAMPLE 41

Racemic (8R*,9aS*)-8-(2-Aminoethyl)-2-(benzo[d]-isoxazol-3-yl)perhydro-1H-pyrido[1,2-a]pyrazine By the method of Example 7, the nitrile title product of Example 40 (700 mg, 2.36 mol) was reduced to afford present title product (610 mg, 86% yield) isolated as a yellow oil. In this product, the 8- and 9a-hydrogen substituents are still cis. TLC Rf (ethyl acetate/methanol/concentrated aqueous ammonia = 1:1:0.15 in volume; potassium permanganate spray): 0.14.

EXAMPLE 42

Racemic (8R*,9aS*)-2-(Benzo[d]isoxazol-3-yl)perhydro-8-(2,2-di(methoxycarbonyl) ethyl)-1H-pyrido[1,2-a]pyrazine By the method of Example 23, the mesylate title product of Example 39 (19.0 g, 52 mmol) was transformed into the present dimethyl malonate-substituted title product (7.80 g, 37% yield) isolated as a viscous yellow oil. TLC Rf (methylene chloride/methanol = 9:1; potassium permanganate spray): 0.54.

EXAMPLE 43

Racemic (8R*,9aS*)-2-(Benzo[d]isoxazol-3-yl)perhydro-8-(3-hydroxypropyl)-1H-pyrido[1,2-a]pyrazine By the method of Example 24, dimethyl malonate-substituted title product of Example 42 (6.34 g, 16 mmol) was converted to the present alcohol title product (0.95 g, 18.8% yield) isolated as a viscous yellow oil. TLC Rf (ethyl acetate/methanol/concentrated aqueous ammonia = 1:1:0.15 in volume; potassium permanganate spray): 0.64.

EXAMPLE 44

Racemic (8R*,9aS*)-2-(Benzo[d]isoxazol-3-yl)perhydro-8-(3-(methanesulfonyloxy-propyl)-1H-pyrido[1,2-a]pyrazine By the method of Example 5, the alcohol title product of Example 43 (0.95 g, 3.01 mmol) was converted into present title product (0.89 g, 75% yield) isolated as a yellow oil. TLC Rf (methylene chloride/methanol = 9:1 in volume; potassium permanganate spray): 0.50.

Final imide-substituted products (having 8- and 9a-hydrogen atoms cis) were obtained by reacting this mesylate with the appropriate sodium imide by the method of Example 17.

EXAMPLE 45

Racemic (7S*,9aS*)-2-(Benzo[d]isoxazol-3-yl)perhydro-7-(hydroxymethyl)-1H-pyrido[1,2-a]pyrazine A mixture consisting of racemic (7S*,9aS*)-7-(hydroxymethyl)perhydro-1H-pyrido[1,2-a]pyrazine (see Example 27; 500 mg, 2.93 mmol), 3-chloro-1,2-benzisoxazole (890 mg, 5.86 mmol) and 1,8-diazabicyclo[5.4.0]-undec-7-ene (DBU, 446 mg, 0.438 ml, 2.93 mmol) in 2,6-lutidine (0.5 ml) was stirred and heated at 145° C. for 18 hours. The solvent was removed in vacuo, and the tarry residue was thoroughly extracted with methylene chloride (150 ml). Insolubles were filtered and the solvent was removed in vacuo to afford a dark brown residue. Flash chromatography of the entire sample (20 g silica gel, 32–63 mesh; eluting with ethyl acetate/methanol=95:5 in volume) afforded 350 mg (41.7%) of the title compound (in which the 7- and 9a-hydrogen substituents remain cis) as a colorless amorphous solid. HRMS m/z 287.1639 (M, $C_{16}H_{21}N_3O_2$). $^{13}$CNMR (CDCl$_3$) delta 164.0, 161.0, 129.5, 122.3, 122.1, 116.1, 110.5, 67.5, 60.2, 58.2, 54.2, 53.7, 48.3, 34.4, 26.9, 26.3.

EXAMPLE 46

Racemic (7S*,9aS*)-2-(Benzo[d]isoxazol-3-yl)perhydro-7-(methanesulfonyloxy)-methyl)-1H-pyrido[1,2-a]pyrazine By the method of Example 5, the title alcohol product of Example 45 (8.0 g, 27.8 mmol) was converted to the present mesylate intermediate (9.57 g, 94.2% yield) isolated as a yellow amorphous solid. TLC Rf (methylene chloride/methanol=9:1 in volume; potassium permanganate spray): 0.76. $^{13}$CNMR (CDCl$_3$) delta 163.9, 161.0, 129.5, 122.3, 122.2, 116.1, 110.4, 71.1, 60.2, 55.7, 54.0, 53.6, 48.3, 37.1, 33.4, 24.7, 24.2.

EXAMPLE 47

Racemic (7R*,9aS*)-2-(Benzo[d]isoxazol-3-yl)-7-(cyanomethyl)-perhydro-1H-pyrido[1,2-a]pyrazine By the method of Example 6, title mesylate product of Example 46 (3.39 g, 9.28 mmol) was converted to the present nitrile title product (1.5 g, 54.5% yield) isolated as a colorless solid. TLC Rf (methylene chloride/methanol=9:1 in volume; potassium permanganate spray): 0.72. $^{13}$CNMR (CDCl$_3$) delta 163.9, 161.0, 129.5, 122.3, 122.1, 119.7, 116.1, 110.4, 60.1, 59.4, 53.9, 53.6, 48.3, 31.2, 26.8, 24.1, 19.5.

EXAMPLE 48

Racemic (7R*,9aS*)-7-(2-Aminoethyl)-2-(benzo[d]-isoxazol-3-yl)perhydro-1H-pyrido[1,2-a]pyrazine By the method of Example 7, title nitrile product of Example 47 (1.50 g, 5.06 mmol) was reduced to the present title amine (1.34 g, 88.2% yield) isolated as a viscous yellow oil. TLC Rf (ethyl acetate/methanol/-concentrated aqueous ammonia=1:1:0.15 in volume; potassium permanganate spray): 0.20.

Final imide-substituted products, having 7- and 9a-hydrogen substituents cis, are realized by reacting this amine product with appropriate acid anhydrides by the methods of Examples 10–12.

EXAMPLE 49

Racemic (7R*,9aS*)-2-(Benzo[d]isoxazol-3-yl)perhydro-7-(2,2-di(methoxycarbonyl)-ethyl)-1H-pyrido[1,2-a]pyrazine By the method of Example 23, mesylate title product of Example 46 (9.57 g, 26 mmol) was converted into the present dimethyl malonate derivative (6.54 g, 61.5% yield) isolated as a light yellow oil. TLC Rf (methylene chloride/methanol=9:1 in volume; potassium permanganate spray): 0.67. $^{13}$CNMR (CDCl$_3$) delta 170.1, 169.9, 163.9, 161.1, 129.4, 122.2(2), 116.2, 110.4, 60.5, 58.7, 54.2, 53.6, 52.5, 50.1, 48.2, 31.3, 30.2, 27.2, 24.5.

EXAMPLE 50

Racemic (7R*,9aS*)-2-(Benzo[d]isoxazol-3-yl)perhydro-7-(3-hydroxypropyl)-1H-pyrido[1,2-a]pyrazine By the method of Example 24, the dimethyl malonate title product of Example 49 (6.54 g, 16 mmol) was converted into present title alcohol (897 mg, 17.7% yield) isolated as a light yellow amorphous solid. TLC Rf (ethyl acetate/methanol/concentrated aqueous ammonia=1:1:0.15; potassium permanganate spray): 0.71.

EXAMPLE 51

Racemic (7R*,9aS*)-2-(Benzo[d]isoxazol-3-yl)perhydro-7-(3-(methanesulfonyloxy)-propyl)-1H-pyrido[1,2-a]pyrazine By the method of Example 5, alcohol title product of Example 50 (897 mg, 2.85 mmol) was converted into the present title mesylate (1.02 g, 90.5% yield) isolated as a viscous yellow oil. TLC Rf (ethyl acetate; potassium permanganate spray): 0.35.

EXAMPLE 52

Using the methods of the preceding Examples additional cis-7-substituted compounds of the formula

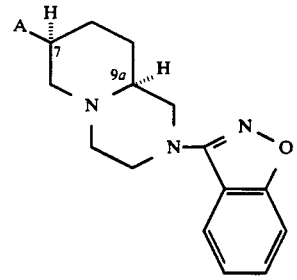

were prepared as follows:

| (±)/(−) | A | Examples[a] | Yield | Properties[b] |
|---|---|---|---|---|
| (±) | (4-(4-fluorobenzoyl)piperidino)methyl | 46/22 | 17% | Rf 0.35(9:1 CH$_2$Cl$_2$:MeOH) |

-continued

| (±)/(−) | A | Examples[a] | Yield | Properties[b] |
|---|---|---|---|---|
| (±) | 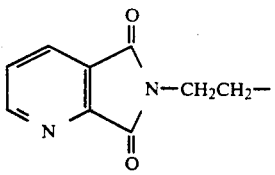 | 48/10 | 17% | Rf 0.24(ethyl acetate) |
| (±) | 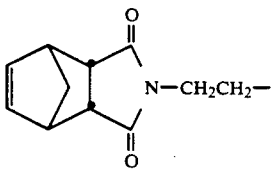 | 48/11, 12 | 5.5% | Rf 0.36(ethyl acetate)<br>HRMS 446.2334 |
| (±) | 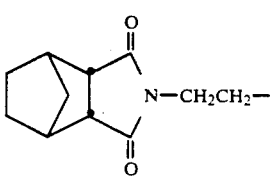 | 48/11, 12 | 20% | Rf 0.5(9:1 $CH_2Cl_2$:MeOH)<br>HRMS 448.2471 |
| (±) | 2-(2,2-dimethylglutarimido)ethyl | 48/11, 12 | 7% | Rf 0.33(ethyl acetate)<br>HRMS 424.2479 |
| (±) | (thiazolidine-2,4-dione-3-yl)methyl | 46/17 | 14% | Rf 0.14(ethyl acetate)<br>HRMS 386.1410 |
| (±) | (3,3-tetramethyleneglutarimido)methyl | 46/17 | 55% | Rf 0.10(ethyl acetate)<br>HRMS 436.2490 |
| (±) | 2-(succinimido)ethyl | 48/10 | 4.9% | Rf 0.18(ethyl acetate) |
| (±) | 2-(3,3-tetramethyleneglutarimido)ethyl | 48/11, 12 | 34% | Rf 0.26(9:1 $CH_2Cl_2$:MeOH)<br>HRMS 450.2632 |
| (±) | 3-(3,3-pentamethyleneglutarimido)propyl | 51/17 | 6% | Rf 0.5(ethyl acetate)<br>HRMS 478.2924 |
| (±) | 2-(2,2-dimethylglutarimido)ethyl | 48/11, 12 | 21% | Rf 0.33(ethyl acetate)<br>HRMS 424.2479 |
| (±) | 2-(cyclopropylcarbonylamino)ethyl | 48/15 | 20% | Rf 0.30(9:1 $CH_2Cl_2$:MeOH)<br>HRMS 368.2167 |
| (±) | 2-(cyclohexylcarbonylamino)ethyl | 48/15 | 15% | Rf 0.47(9:1 $CH_2Cl_2$:MeOH)<br>HRMS 410.2702 |
| (±) | 2-(cyclopentylmethylcarbonylamino)ethyl | 48/15 | 10% | Rf 0.40(9:1 $CH_2Cl_2$:MeOH)<br>HRMS 410.2668 |
| (±) | 2-(cyclohexylmethylcarbonylamino)ethyl | 48/15 | 28% | Rf 0.40(9:1 $CH_2Cl_2$:MeOH)<br>HRMS 424.2848 |
| (±) | 2-(cyclopentylcarbonylamino)ethyl | 48/15 | 15% | Rf 0.33(9:1 $CH_2Cl_2$:MeOH)<br>HRMS 396.2510 |
| (±) | 2-(cyclobutylcarbonylamino)ethyl | 48/15 | 16% | Rf 0.31(9:1 $CH_2Cl_2$:MeOH)<br>HRMS 382.2369 |
| (±) | 2-(benzoylamino)ethyl | 48/15 | 7.4% | Rf 0.48(9:1 $CH_2Cl_2$:MeOH) |
| (±) | 2-(4-(cyclohexyl)butyryl)amino)ethyl | 48/15 | 6.6% | Rf 0.42(9:1 $CH_2Cl_2$:MeOH)<br>HRMS 452.3157 |
| (±) | 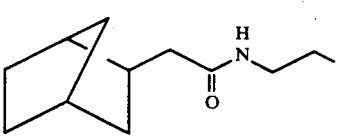 | 48/15 | 19% | Rf 0.41(9:1 $CH_2Cl_2$:MeOH)<br>HRMS 436.2846 |

[a]Source of Starting Material/Coupling Method(s)
[b]Rf values are for thin layer chromatography (TLC) on silica gel with $KMnO_4$ spray;
HRMS = high resolution mass spectrum, observed values are for the mass ion and are very close to theoretical.

EXAMPLE 53

Using the methods of the preceding Examples additional trans-7-substituted compounds of the formula were prepared as follows:

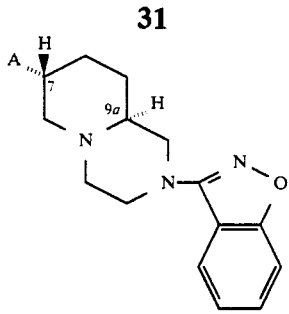

| (±)/(−) | A | Examples[a] | Yield | Properties[b] |
|---|---|---|---|---|
| (±) | [spiro-dioxolane-piperidine-N-CH2-] | 5/22 | 29% | Rf 0.63(9:1 CH2Cl2:MeOH) HRMS 412.2483 |
| (±) | [camphor imide N-CH2-][c] | 5/17 | 28% | Rf 0.53(9:1 CH2Cl2:MeOH) HRMS 450.2635 |
| (±) | [norbornene dicarboximide N-CH2-] | 5/17 | 28% | Rf 0.26(ethyl acetate) HRMS 432.2141 |
| (±) | [camphorsultam N-CH2-][d] | 5/17 | 13% | Rf 0.45(ethyl acetate) HRMS 484.2498 |
| (±) | [cyclopentane thia imide N-CH2-] | 5/17 | 73% | Rf 0.76(ethyl acetate) HRMS 440.1849 |
| (+) | 2-(3,3-tetramethyleneglutarimido)ethyl | 9/11, 12 | 55% | Rf 0.25(ethyl acetate) HRMS 450.2639 |
| (±) | 3-(3,3-tetramethyleneglutarimido)propyl | 24/17 | 24% | Rf 0.47(9:1 CH2Cl2:MeOH) |
| (±) | 2-(3,3-pentamethyleneglutarimido)ethyl | 7/11, 12 | 20% | Rf 0.61(9:1 CH2Cl2:MeOH) HRMS 464.2792 |
| (±) | (2,2-dimethylglutarimido)methyl | 19/11, 12 | 14% | Rf 0.39(9:1 CH2Cl2:MeOH) HRMS 410.2306 |
| (±) | 2-(cyclopentylcarbonylamino)ethyl | 7/21 | 22% | Rf 0.46(9:1 CH2Cl2:MeOH) HRMS 396.2523 |
| (−) | 2-(cyclopentylcarbonylamino)ethyl | 8/16 | 61% | Rf 0.43(9:1 CH2Cl2:MeOH) HRMS 396.2528 $[\alpha]_D^{20}$ = −3.63 (c = 1.1, CH2Cl2) |
| (−) | 2-(cyclopentylacetylamino)ethyl | 8/15 | 29% | Rf 0.49(9:1 CH2Cl2:MeOH) HRMS 410.2692 |
| (−) | 2-(cyclohexylcarbonylamino)ethyl | 8/16 | 24% | Rf 0.45(9:1 CH2Cl2:MeOH) HRMS 410.2695 $[\alpha]_D^{20}$ = −2.92 (c = 0.41, CH2Cl2) |

| (±)/(−) | A | Examples[a] | Yield | Properties[b] |
|---|---|---|---|---|
| (=) | 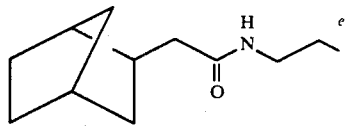 [e] | 7/15 | 16% | Rf 0.6(9:1 CH$_2$Cl$_2$:MeOH) HRMS 436.2834 |
| (±) | 2-((phenylacetyl)amino)ethyl | 7/15 | 14% | Rf 0.39(9:1 CH$_2$Cl$_2$:MeOH) HRMS 418.2363 |
| (±) | 2-(cycloheptylcarbonylamino)ethyl | 7/15 | 27% | Rf 0.47(9:1 CH$_2$Cl$_2$:MeOH) HRMS 424.2829 |
| (−) | 2-(cycloheptylcarbonylamino)ethyl | 8/15 | 62% | Rf 0.47(9:1 CH$_2$Cl$_2$:MeOH) HRMS 424.2821 $[\alpha]_D^{20}$ = −3.14 (c = 1.05, CH$_2$Cl$_2$) |
| (±) | 2-(cyclobutylcarbonylamino)ethyl | 7/15 | 17% | Rf 0.41(9:1 CH$_2$Cl$_2$:MeOH) HRMS 382.2346 |
| (±) | 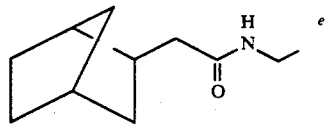 [e] | 19/21 | 13% | Rf 0.56(9:1 CH$_2$Cl$_2$:MeOH) HRMS 422.2695 |
| (±) | 2-(3-cyclohexylpropionylamino)ethyl | 7/15 | 37% | Rf 0.46(9:1 CH$_2$Cl$_2$:MeOH) HRMS 438.3002 |
| (±) | 2-(3-cyclopentylpropionylamino)ethyl | 7/15 | 14% | Rf 0.36(9:1 CH$_2$Cl$_2$:MeOH) HRMS 424.2852 |

[a]Source of Starting Material/Coupling Method(s)
[b]Rf values are for thin layer chromatography (TLC) with KMnO$_4$ spray;
HRMS = high resolution mass spectrum, observed values are for the mass ion and are very close to theoretical.
[c]Reactant from (1R, 3S)-(+)-camphoric acid.
[d]Reactant from D-(−)-2,10-camphorsultam.
[e]Reactant from 2-norbornane-acetic acid.

EXAMPLE 54

Using the methods of the preceding Examples additional cis-8-substituted compounds of the formula

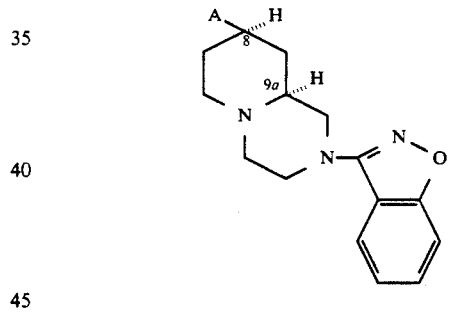

were prepared as follows:

| (±)/(−) | A | Examples[a] | Yield | Properties[b] |
|---|---|---|---|---|
| (±) | 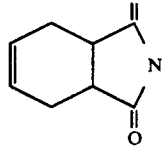 | 39/17 | 10% | Rf 0.11(ethyl acetate) HRMS 420.2145 |
| (±) | (5,5-tetramethylene-thiazolidine-2,4-dione-3-yl)methyl | 39/17 | 75% | Rf 0.38(ethyl acetate) HRMS 440.1861 |
| (±) | 2-(3,3-tetramethylene-glutarimido)ethyl | 41/10 | 20% | Rf 0.19(ethyl acetate) HRMS 450.2631 |
| (±) | 3-(3,3-tetramethylene-glutarimido)propyl | 44/17 | 20% | Rf 0.31(19:1 ethyl acetate:MeOH) HRMS 464.2799 |
| (±) | 3-(3,3-pentamethylene-glutarimido)propyl | 44/17 | 24% | Rf 0.47(9:1 CH$_2$Cl$_2$:MeOH) HRMS 478.2945 |
| (±) | 3-(3,3-trimethylene-glutarimido)propyl | 44/17 | 4.6% | Rf 0.26(ethyl acetate) HRMS 450.2610 |
| (±) | (3,3-tetramethylene- | 39/17 | — | Rf 0.59(ethyl acetate) |

| (±)/(−) | A | Examples[a] | Yield | Properties[b] |
|---|---|---|---|---|
| | glutarimido)methyl | | | HRMS 436.2461 |

[a]Source of Starting Material/Coupling Method(s)
[b]Rf values are for thin layer chromatography (TLC) with KMnO4 spray;
HRMS = high resolution mass spectrum, observed values are for the mass ion and are very close to the theoretical values.

PREPARATION 1 trans-5-(Methoxycarbonyl)piperidine-2-carboxylic Acid

Dimethyl cis-piperidine-2,5-dicarboxylate (20 g, 0.077 mol), salicylaldehyde (3 ml, about 0.014 mol) and acetic acid (200 ml) were combined and heated at reflux for 24 hours. The mixture was cooled and stripped in vacuo to a thick oil. This residue was taken up in 300 ml of isopropyl alcohol and restripped to 200 ml, by which time product began to precipitate. After granulating for 2 hours, title product was recovered by filtration and air dried, 9.20 g; m.p. 184° C. (softening), 191°-200° C. (dec.); $^1$H-NMR(CDCl$_3$, 300 MHz)delta: 3.73 (s, 3H), 3.62 (septet, 2H), 3.15 (t, 1H), 2.90 (m, 1H), 2.30 (m, 2H), 1.74 (m, 2H).

Crude cis-5-(methoxycarbonylpiperidine-2-carboxylic acid, containing some additional amount of the trans-isomer, 4.52 g, was recovered by stripping mother liquors. This material is suitable for recycling in the present process in place of dimethyl cis-piperidine-2,5-dicarboxylate.

Substitution of benzaldehyde for salicylaldehyde gave the same products, but the desired equilibrium mixture of cis and trans acids was achieved more slowly.

PREPARATION 2

3:1 Mixture of trans and cis-5-(Methoxycarbonyl)piperidine-2-carboxylic Acid

Dimethyl cis-piperidine-2,5-dicarboxylate (112 g, 0.56 mol), salicylaldehyde (3 ml, 0.056 mol) and glacial acetic acid (600 ml) were combined and the resulting mixture heated at about 100° C. for 60 hours. The mixture was cooled, than stripped in vacuo to a thick oil from which 61.7 g (59%) of title products crystallized upon stirring with 800 ml of isopropyl alcohol. Product ratio was determined by $^1$H-NMR (D$_2$O, 300 MHz), a peak at 3.13 ppm (t, 1H, J=14.5 Hz) being diagnostic of trans, and a peak at 3.33 ppm (dd, 1H) being diagnostic of cis.

PREPARATION 3

Dimethyl trans-Piperidine-2,5-dicarboxylate Hydrochloride

Method A

Title product mixture of the preceding Preparation (15.1 g, 0.08 mol) was suspended in 200 ml of methanol and stirred under N$_2$ at 0°-5° C. Thionyl chloride (7.35 ml, 0.1 mol) was added dropwise over about 5 minutes. After 30 minutes the mixture was warmed to room temperature, and after 1 hour warmed to reflux for 6 hours. Upon cooling title product (6.8 g) crystallized from the reaction mixture. A second and third crop (5.3 g and 0.63 g) were obtained by stripping mother liquors to low volume and diluting to 200 ml with isopropyl alcohol. The combined yield of present title product was 67%; m.p. 207°-209° C.

Analysis calculated:
C, 45.48; H, 6.79; N, 5.89.
Found: C, 45.34; H, 6.55; N, 5.82.
Dimethyl cis-piperidine-2,5-dicarboxylate recoverable from mother liquors is recycled as starting material in Preparation 1 or 2 above.

Method B

In like manner, title product of Preparation 1 is converted to present title product.

PREPARATION 4

70:30 Mixture of Racemic (7S*,9aS*)-7-(Hydroxymethyl)perhydro-1H-pyrido[1,2-a]pyrazine and Racemic (7R*,9aS*)-7-(Hydroxymethyl)-perhydro-1H-pyrido[1,2-a]pyrazine By the methods of Preparations 1-4 at pages 26-27 of International Patent Application No. WO 90/08144, dimethyl pyridine-2,5-dicarboxylate was converted to a mixture of racemic methyl 1-oxoperhydro-1H-pyrido[1,2-a]-pyrazine-7-carboxylates as an oil (i.e., without separation by crystallization of the "cis" or (7S*,9aS*)isomer). LiAlH$_4$ reduction of this mixture according to Preparation 5 at page 28 of said WO 90/08144 afforded present title products in nearly quantitative yield. The product ratio was estimated by 300 MHz $^1$H-NMR.

PREPARATION 5

Racemic Dimethyl cis-Pyridine-2,4-dicarboxylate

A solution of pyridine-2,4-dicarboxylic acid dimethyl ester (148.5 g, 0.76 mol) in ethyl acetate (1.5 liters) was hydrogenated at ambient temperature on a Parr apparatus (50 psig hydrogen pressure over 4.0 g; platinum oxide catalyst) for 18 hours. The catalyst was filtered and the filtrate was concentrated in vacuo to a yellow oil. The oil was dissolved in a well-stirred methylene chloride/water mixture (4 liters and 1 liter, respectively) with pH adjusted to 9.5 (sodium carbonate). The layers were separated, and the aqueous portion was extracted twice with 1 liter portions of fresh methylene chloride. The combined organic extracts were dried (anhydrous sodium sulfate) and concentrated in vacuo to a viscous yellow oil. The above procedure was repeated on the same scale and the title product from both runs were combined (290.1 g, 94.7% yield). TLC Rf (methylene chloride/methanol=9:1 in volume; potassium permanganate spray): 0.36. (Rf of dimethyl ester starting material in the same system: 0.82).

PREPARATION 6

Dimethyl cis-N-(2-(phthalimido)ethyl)-piperidine-2,5-dicarboxylate

Method A

A solution of 12.0 g (45.6 mmol) phthalimido acetaldehyde diethyl acetal (Aldrich Chemical Co., Inc.) in 36 ml acetic acid and 1.34 ml concentrated HCl was heated at 45°-50° C. for 2 hours. After cooling the solution to 20° C., 9.08 g dimethyl cis-piperidine-2,5-dicarboxylate was added and stirring was continued for an additional 30 minutes at 20°-25° C. The resulting light orange solution was treated with the portionwise addition of 12.08 g (57 mmol) Na(OAc)$_3$BH over 30 minutes and stirred for an additional 30 minutes at 30°-35° C. The solution was cooled to 20° C. and diluted with 120 ml H$_2$O and 120 ml CH$_2$Cl$_2$ followed by shaking and separation of the phases. The organic phase was washed first with 50 ml H$_2$O and then 50 ml saturated NaHCO$_3$. Displacement of the CH$_2$Cl$_2$ with 36 ml EtOH followed by the addition of 100 ml hexanes resulted in the crystallization of a solid which was allowed to granulate overnight at 20°-25° C. Filtration and drying of this solid provided 13.5 g (79.4%) of present title product as a solid melting at 97°-100° C.

Method B

A stirred mixture of 70 ml of CH$_2$Cl$_2$, 9.8 g (51 mmol) of N-(2-hydroxyethyl)phthalimide and 6.1 ml (0.52 mmol) of 2,6-lutidine was cooled to −4° C. Maintaining the temperature below 15° C., trifluoromethane sulfonic anhydride (8.9 ml, 0.53 mmol) was added slowly over 1 hour. The resulting mixture was stirred at 15°-20° C. for 1.25 hours, then washed sequentially with 40 ml H$_2$O, 40 ml 2N HCl and 40 ml H$_2$O to yield a solution of N-((2-triflyloxy)ethyl)phthalimide. At 20°-25° C., a separate reaction vessel was charged with 50 ml CH$_2$Cl$_2$, 55 ml H$_2$O and 10.6 g (0.1 mol) Na$_2$CO$_3$. After stirring for 15 minutes, dimethyl cis-piperidine-2,5-dicarboxylate (11.9 g, 50 mmol) and the above reagent solution were added, and the mixture stirred for 1.25 hours at 20°-25° C. The organic layer was separated, washed with 30 ml of water, and the CH$_2$Cl$_2$ displaced by boiling with hexane to a final volume of 125 ml, during which present title product began to crystallize. After stirring and granulating for 1 hour at 0°-5° C., present title product, 16.7 g, was recovered by filtration; m.p. 98°-100° C.

Method C

To a well-stirred bi-phasic mixture consisting of sodium carbonate (500 g, 4.72 mol) in water (3 liters) and cis-2,5-piperidine dicarboxylate dimethyl ester (240 g, 1.18 mol) in methylene chloride (4.5 liters), a solution of 2-phthalimido-ethanol triflate (417 g, 1.29 mol) in methylene chloride (3 liters) is added in a steady stream over a 3 hour period. The organic layer is separated, and the aqueous layer is extracted with fresh methylene chloride (3 liters). The combined organic extracts are washed with water (3 liters), then with brine (3 liters), dried with anhydrous magnesium sulfate and finally concentrated in vacuo to a solid. The entire residue is triturated in refluxing ether (3 liters) with vigorous stirring for 15 minutes. After cooling to ambient temperature, the solution is poured into hexanes (3 liters), and the resulting mixture is stirred for 18 hours. Title product is collected by filtration.

PREPARATION 7

Methyl (7S*,9aS*)-4,6,7,8,9,9a-Hexahydro-2H,3H-pyrido[1,2-a]pyrazin-1-one-7-carboxylate A mixture of 240 ml of methanol, 16.6 g (44 mmol) of title product of Preparation 6, and 5.74 ml (97 mmol) of 54% hydrazine was stirred at 20°-25° C. for 17 hours. The mixture was then diluted with 200 ml of CH$_2$Cl$_2$, granulated for 1 hour, and diimide by-product recovered by filtration with 75 ml CH$_2$Cl$_2$ wash. The combined filtrate and wash liquor was concentrated to 225 ml by distillation and CH$_2$Cl$_2$/methanol displaced with isopropyl alcohol to a final volume of 200 ml. After cooling slowly from 50° C. to 8° C. over a 2 hour period, title product, 9.2 g, was recovered by filtration. The entire batch was purified by recrystallization from CH$_2$Cl$_2$ to yield 7.45 g of purified title product, identical with the product of Preparation 4 of above cited Bright et al., W090/08144.

I claim:

1. A racemic or optically active perhydro-1H-pyrido[1,2-a]pyrazine having the formula

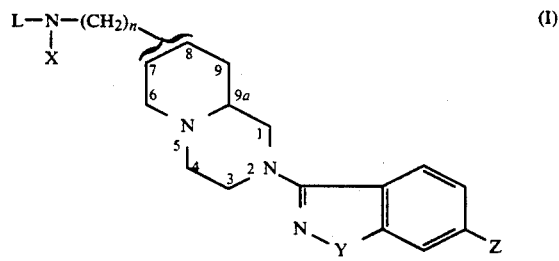

wherein

Z is H or Cl;

Y is O or S;

n is 1, 2, 3 or 4; and

L and X are taken separately, X is H or (C$_1$-C$_2$)alkyl and L is R(CH$_2$)$_m$CO where m is 0, 1, 2 or 3 and R is (C$_1$-C$_6$)alkyl, (C$_3$-C$_7$)cycloalkyl, phenyl, naphthyl, furyl, benzofuranyl, thienyl, benzothienyl, pyrrolyl, indolyl, isoindolyl, norbornylmethyl, or one of said groups substituted on aromatic or heteroaromatic ring with fluoro, chloro, (C$_1$-C$_2$)alkyl or (C$_1$-C$_2$)alkoxy; or L and X are taken together and are:

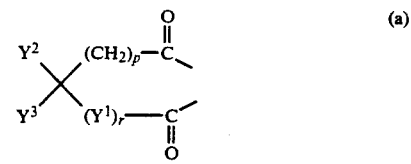

where Y$^1$ is CH$_2$, S, O or NH; Y$^2$ and Y$^3$ are taken separately and Y$^2$ and Y$^3$ are each independently hydrogen or methyl, or Y$^2$ and Y$^3$ are taken together and are (CH$_2$)$_q$; p is 1 or 2, q is 2, 3, 4 or 5; and r is 0 or 1;

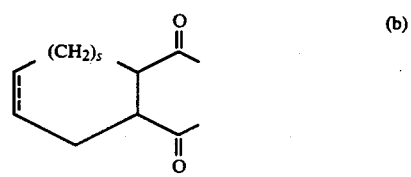

where s is 0 or 1; and - - - represents a bond or no bond;

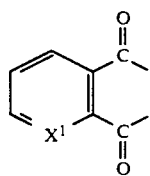
(c)

where X¹ is CH or N;

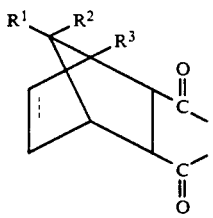
(d)

where R¹, R² and R³ are each independently H or CH₃ and - - - represents a bond or no bond;

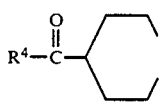
(e)

where R⁴ is phenyl or phenyl substituted with F, Cl, (C₁-C₂)alkyl or (C₁-C₂)alkoxy;

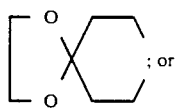
(f)

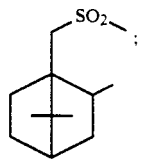
(g)

or a pharmaceutically acceptable acid addition salt thereof.

2. A compound of claim 1 wherein the group

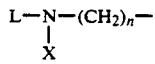

is attached at the 7-position of pyridopyrazine ring system.

3. A compound of claim 2 wherein Y is O and Z is H.

4. A compound of claim 3 wherein L and X are taken separately.

5. A compound of claim 4 wherein X is hydrogen.

6. A compound of claim 5 wherein the hydrogen substituted at the 7-position of the pyridopyrazine ring system is trans to the 9a-hydrogen.

7. A compound of claim 6 wherein R is (C₃-C₇)-cycloalkyl or phenyl and m is 0 or 1.

8. A compound of claim 7 wherein n is 2 and R is cyclopentyl.

9. A compound of claim 7 wherein n is 2 and R is cyclohexyl.

10. A compound of claim 7 wherein n is 2 and R is cycloheptyl.

11. An optically active compound of claim 7.

12. A compound of claim 11 wherein n is 2 having 7S,9aS-stereochemistry.

13. The compound of claim 12 wherein m is 0 and R is cyclopentyl.

14. The compound of claim 12 wherein m is 0 and R is cyclohexyl.

15. The compound of claim 12 wherein m is 0 and R is cycloheptyl.

16. A compound of claim 5 wherein the hydrogen substituted at the 7-position of the pyridopyrazine ring system is cis to the 9a-hydrogen.

17. A compound of claim 16 wherein R is (C₃-C₆)-cycloalkyl or phenyl and m is 0 or 1.

18. A compound of claim 17 wherein n is 2.

19. A compound of claim 18 wherein m is 1 and R is cyclopentyl.

20. A compound of claim 18 wherein m is 0.

21. A compound of claim 20 wherein R is cyclopropyl.

22. A compound of claim 20 wherein R is cyclobutyl.

23. A compound of claim 20 wherein R is cyclopentyl.

24. A compound of claim 20 wherein R is cyclohexyl.

25. A compound of claim 20 wherein R is phenyl.

26. A compound of claim 3 wherein L and X are taken together.

27. A compound of claim 26 wherein L and X are

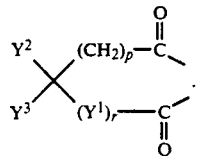

28. A compound of claim 27 wherein the hydrogen substituted at the 7-position of the pyridopyrazine ring system is trans to the 9a-hydrogen.

29. A compound of claim 28 wherein n is 1 or 2, p and r are each 1, Y¹ is CH₂, and Y² and Y³ are taken together.

30. A compound of claim 29 wherein n is 1.

31. A compound of claim 30 wherein q is 4.

32. A compound of claim 29 wherein n is 2.

33. A compound of claim 32 wherein q is 3.

34. A compound of claim 32 wherein q is 4.

35. An optically active compound of claim 28 wherein n is 2.

36. A compound of claim 35 having 7S,9aS-stereochemistry.

37. A compound of claim 36 wherein p and r are each 1, Y¹ is CH₂, and Y² and Y³ are taken together.

38. The compound of claim 37 wherein q is 3.

39. The compound of claim 37 wherein q is 4.

40. A compound of claim 27 wherein the hydrogen substituted at the 7-position of the pyridopyrazine ring system is cis to the 9a-hydrogen.

41. A compound of claim 40 wherein n is 2.

42. A compound of claim 41 wherein p is 2, r is 0 and Y² and Y³ are taken separately and are each methyl.

43. A compound of claim 26 wherein L and X are $$\underset{R^1\phantom{xx}R^2}{\overset{R^3}{\diagup}}\text{(bicyclic structure with two C=O groups)}$$

44. A compound of claim 43 wherein - - - is not a bond, and $R^1$, $R^2$ and $R^3$ are each hydrogen.

45. A compound of claim 44 wherein n is 2 and the group substituted at the 7-position of the pyridopyrazine ring system is trans to the 9a-hydrogen.

46. A compound of claim 1 wherein the group $$L-\underset{X}{\overset{|}{N}}-(CH_2)_n-$$

is attached at the 8-position of the pyridopyrazine ring system, and is trans to the 9a-hydrogen; Z is hydrogen and Y is O.

47. A compound of claim 46 wherein L and X are taken separately and X is hydrogen.

48. A compound of claim 46 wherein L and X are taken together.

49. A compound of claim 48 wherein L is $$\begin{array}{c} Y^2 \diagdown \phantom{x}(CH_2)_p-\overset{O}{\overset{\|}{C}}\diagdown \\ Y^3 \diagup \phantom{x}(Y^1)_r-\underset{\|}{\overset{\phantom{.}}{C}}\diagup \\ \phantom{xxxxxxxx}O \end{array}$$

50. A compound of claim 49 wherein $Y^1$ is $CH_2$, p and r are each 1, and $Y^2$ and $Y^3$ are taken together.

51. A compound of claim 50 wherein n is 2 and q is 4.

52. A pharmaceutical composition for the treatment of psychotic disorders which comprises a neuroleptic effective amount of a compound of claim 1 and a pharmaceutically acceptable carrier.

53. A pharmaceutical composition for the treatment of psychotic disorders which comprises a neuroleptic effective amount of a compound of claim 2 and a pharmaceutically acceptable carrier.

54. A method of treating psychotic disorders which comprises administering to a psychotic patient in need of such treatment a neuroleptic effective amount of a compound of claim 1.

55. A method of treating psychotic disorders which comprises administering to a psychotic patient in need of such treatment a neuroleptic effective amount of a compound of claim 2.

56. A method of treating psychotic disorders which comprises administering to a psychotic patient in need of such treatment a neuroleptic effective amount of a compound of claim 12.

57. A method of treating psychotic disorders which comprises administering to a psychotic patient in need of such treatment a neuroleptic effective amount of a compound of claim 36.

58. A racemic or optically active perhydro-1H-pyrido[1,2-a]pyrazine having the formula $$Z_1-(CH_2)_n-\text{(perhydropyrido[1,2-a]pyrazine attached to benzisoxazole with Y and Z substituents)}$$

wherein

Z is H or Cl;

Y is O or S;

n is 1, 2, 3 or 4; and $Z^1$ is NHX, OH, $OSO_2R^5$, $N_3$, CN or $$\begin{array}{c} Y^2 \diagdown \phantom{x}(CH_2)_p-\overset{O}{\overset{\|}{C}}NH- \\ Y^3 \diagup \phantom{x}(Y^1)_r-\underset{\|}{\overset{\phantom{.}}{C}}OH \\ \phantom{xxxxxxxx}O \end{array}$$ ;

X is hydrogen or $(C_1-C_2)$alkyl;

$Y^2$ and $Y^3$ are taken separately and $Y^2$ and $Y^3$ are each independently hydrogen or methyl; or $Y^2$ and $Y^3$ are taken together and are $(CH_2)_q$;

p is 1 or 2;

q is 2, 3, 4 or 5;

r is 0 or 1; and $R^5$ is $(C_1-C_3)$alkyl, phenyl or tolyl; with the proviso that when $Z^1$ is CN, n is other than 4.

59. A compound of claim 58 wherein Y is O and Z is H.

60. A compound of claim 59 wherein the substituent $Z^1-(CH_2)_n-$ is substituted at the 7-position of the pyridopyrazine ring system.

61. A compound of claim 60 wherein n is 2.

62. A compound of claim 61 wherein $Z^1$ is $NH_2$.

63. A compound of claim 62 wherein the hydrogen substituted at the 7-position is trans to the 9a-hydrogen.

64. An optically active compound of claim 63.

65. The compound of claim 64 having 7S,9aS-stereochemistry.

66. A compound of claim 61 wherein $Z^1$ is $$\begin{array}{c} Y^2 \diagdown \phantom{x}(CH_2)_p-\overset{O}{\overset{\|}{C}}NH- \\ Y^3 \diagup \phantom{x}(Y^1)_r-\underset{\|}{\overset{\phantom{.}}{C}}OH \\ \phantom{xxxxxxxx}O \end{array}$$

67. A compound of claim 66 wherein $Y^2$ and $Y^3$ are taken together, p and r are each 1 and q is 3 or 4.

68. An optically active compound of claim 67 having 7S,9aS-stereochemistry.